(12) United States Patent
Matsuyama

(10) Patent No.: US 7,314,866 B2
(45) Date of Patent: Jan. 1, 2008

(54) KU-70-DERIVED BAX-SUPPRESSING PEPTIDES AND USE THEREOF FOR THE PROTECTION OF DAMAGED CELLS

(75) Inventor: Shigemi Matsuyama, Glendale, WI (US)

(73) Assignee: Bloodcenter of Wisconsin, Inc., Milwaukee, WI (US)

( * ) Notice: Subject to any disclaimer, the term of this patent is extended or adjusted under 35 U.S.C. 154(b) by 543 days.

(21) Appl. No.: 10/375,980

(22) Filed: Feb. 28, 2003

(65) Prior Publication Data

US 2003/0216323 A1 Nov. 20, 2003

Related U.S. Application Data

(60) Provisional application No. 60/384,204, filed on May 30, 2002, provisional application No. 60/360,755, filed on Mar. 1, 2002.

(51) Int. Cl.
- *A61K 38/08* (2006.01)
- *C07K 2/00* (2006.01)
- *C07K 7/04* (2006.01)
- *C07K 5/10* (2006.01)
- *A61K 38/07* (2006.01)

(52) U.S. Cl. ........................ 514/17; 530/329; 530/330; 514/18

(58) Field of Classification Search .................... None
See application file for complete search history.

(56) References Cited

U.S. PATENT DOCUMENTS

| 6,753,151 B1 * | 6/2004 | Jackson et al. ............. 435/7.1 |
| 6,770,656 B2 * | 8/2004 | Halazy et al. ............. 514/307 |
| 2003/0073661 A1 * | 4/2003 | Matsuyama et al. .......... 514/44 |
| 2003/0216323 A1 * | 11/2003 | Matsuyama .................. 514/17 |

FOREIGN PATENT DOCUMENTS

| WO | WO9701635 A1 * | 1/1997 |
| WO | WO98/40397 | 9/1998 |
| WO | WO 0032221 A2 * | 6/2000 |
| WO | WO 0160798 A1 * | 8/2001 |
| WO | WO 03/027237 A2 | 4/2003 |

OTHER PUBLICATIONS

S. Nagpal, et al., "Structure-function Analysis of Tritrypticin, an Antibacterial Peptide of Innate Immune Origin," J. Biol. Chem. 274(33):23296-23304, 1999.
M. Sawada, et al., "Ku70 Suppresses Cell Death by Inhibiting Mitochondrial Translocation of BAX," Proceedings of the 93rd Annual Meeting of the American Association for Cancer Research, San Francisco, CA 43:998, Apr. 6-10, 2002.
M. Sawada, et al., "Cytoprotective Membrane-Permeable Peptides Designed from the Bax-binding Domain of Ku70," Nature, pp. 1-7, 2003.
S.C. Kampranis, et al., "A Novel Plant Glutathione S-Transferase/Peroxidase Suppresses Bax Lethality in Yeast," J. Biol. Chem. 275(38):29207-29216, 2000.
H. Moon, et al., "Soybean Ascorbate Peroxidase Suppresses Bax-induced Apoptosis in Yeast by Inhibiting Oxygen Radical Generation," Biochem. Biophys. Res. Comm. 290:457-462, 2002.
Sawada M & Matsuyama S, Corrigendum,: Nat. Cell. Biol. 6:373-374 (2004).
Matsuyama S, "Retractions," Nat. Cell. Biol. 9:480 (2007).
Pearson H, "Image manipulation: CSI: cell biology," Nature 434:952-953 (2005).
Yoshida T, et al., "Bax-Inhibiting peptide derived from mouse and rat Ku70," Biochem. Biophys. Res. Commun. 321:961-966 (2004).

* cited by examiner

*Primary Examiner*—Cecilia J. Tsang
*Assistant Examiner*—Andrew D. Kosar
(74) *Attorney, Agent, or Firm*—Quarles & Brady LLP

(57) ABSTRACT

A method of protecting cells from cell death comprising the step of supplying to the cell an effective amount of a Bax-inhibiting peptide is disclosed.

11 Claims, 16 Drawing Sheets

| SEQUENCE OF PEPTIDE | ANTI-BAX ACTIVITY |
|---|---|
| VPMLKE (V6) | + |
| VPMLK (V5) | + |
| PMLKE (P5) | + |
| PMLK (P4) | − |
| MLKE (M4) | − |
| IPMIK (NC) | − |
| (NC = NEGATIVE CONTROL) | |

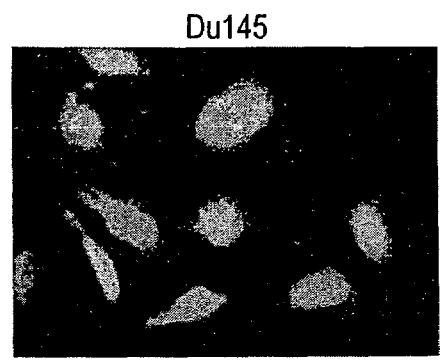
FIG. 5a    FIG. 5b
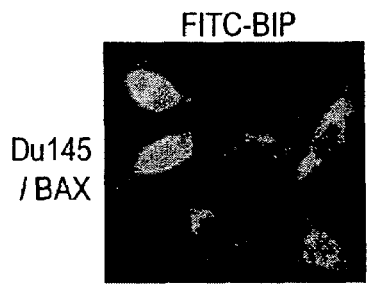
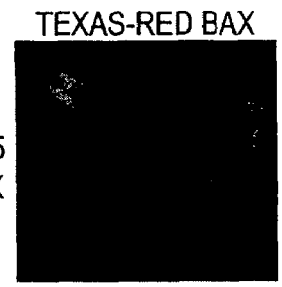
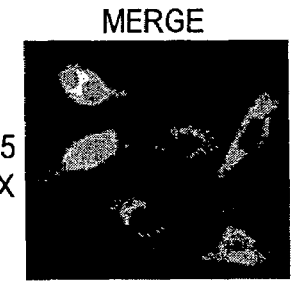
FIG. 5c    FIG. 5d    FIG. 5e
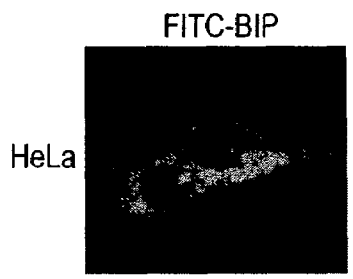
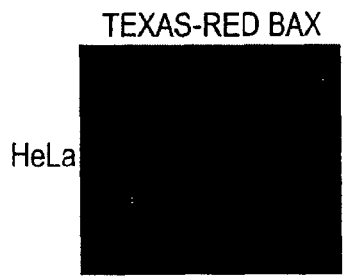
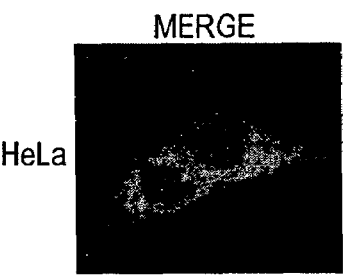
FIG. 5g    FIG. 5h    FIG. 5i
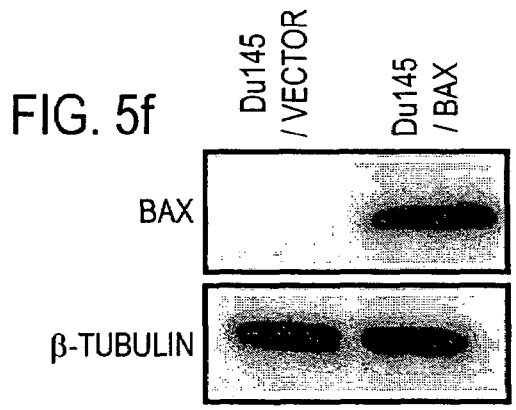
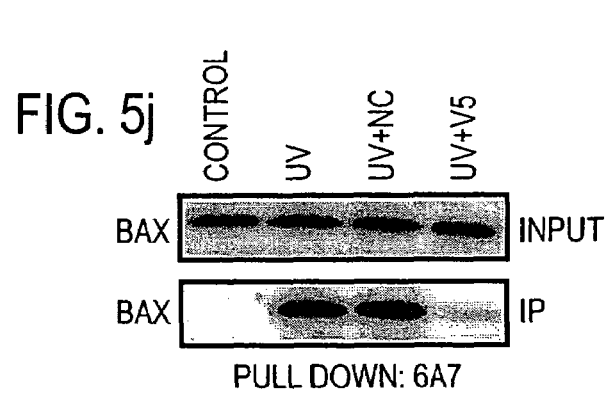
FIG. 5f    FIG. 5j

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial
<220> FEATURE:
<223> OTHER INFORMATION: Synthetic peptide.

<400> SEQUENCE: 1

Val Pro Met Leu Lys
1               5

<210> SEQ ID NO 2
<211> LENGTH: 5
<212> TYPE: PRT
<213> ORGANISM: Artificial
<220> FEATURE:
<223> OTHER INFORMATION: Synthetic peptide.

<400> SEQUENCE: 2

Pro Met Leu Lys Glu
1               5

<210> SEQ ID NO 3
<211> LENGTH: 4
<212> TYPE: PRT
<213> ORGANISM: Artificial
```

```
<220> FEATURE:
<223> OTHER INFORMATION: Synthetic peptide.

<400> SEQUENCE: 3

Pro Met Leu Lys
1

<210> SEQ ID NO 4
<211> LENGTH: 6
<212> TYPE: PRT
<213> ORGANISM: Artificial
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: X is an amino acid with non-polar side chain.
<220> FEATURE:
<221> NAME/KEY: MISC_FEATURE
<222> LOCATION: (3)..(3)
<223> OTHER INFORMATION: X is an amino acid with non-polar side chain.
<220> FEATURE:
<221> NAME/KEY: MISC_FEATURE
<222> LOCATION: (5)..(6)
<223> OTHER INFORMATION: X is an amino acid with charged polar side
      chain.

<400> SEQUENCE: 4

Xaa Pro Xaa Leu Xaa Xaa
1               5

<210> SEQ ID NO 5
<211> LENGTH: 5
<212> TYPE: PRT
<213> ORGANISM: Artificial
<220> FEATURE:
<223> OTHER INFORMATION: Synthetic peptide.

<400> SEQUENCE: 5

Ile Pro Met Ile Lys
1               5

<210> SEQ ID NO 6
<211> LENGTH: 4
<212> TYPE: PRT
<213> ORGANISM: Artificial
<220> FEATURE:
<223> OTHER INFORMATION: Synthetic peptide.

<400> SEQUENCE: 6

Met Leu Lys Glu
1

<210> SEQ ID NO 7
<211> LENGTH: 6
<212> TYPE: PRT
<213> ORGANISM: Artificial
<220> FEATURE:
<223> OTHER INFORMATION: Synthetic peptide.

<400> SEQUENCE: 7

Val Pro Met Leu Lys Glu
1               5
```

KU-70-DERIVED BAX-SUPPRESSING PEPTIDES AND USE THEREOF FOR THE PROTECTION OF DAMAGED CELLS

CROSS-REFERENCE TO RELATED APPLICATION

This application claims priority to U.S. provisional applications 60/360,755 filed Mar. 1, 2002 and filed 60/384,204 filed May 30, 2002 and U.S. application Ser. No. 10/247,045. All three applications are incorporated by reference.

STATEMENT REGARDING FEDERALLY SPONSORED RESEARCH OR DEVELOPMENT

BACKGROUND OF THE INVENTION

Bcl-2 family proteins are known to regulate a distal step in an evolutionarily conserved pathway for programmed cell death, with some members functioning as suppressors of apoptosis and others as promoters of cell death (Gross, et al., *Genes Dev.* 13:1899–1911, 1999; Reed, *Nature* 387:773–776, 1997). In mammalian cells, Bcl-2 family proteins are known to control mitochondria-dependent cell death cascades (Adams and Cory, *Science* 281:1322–1326, 1998; Green and Reed, *Science* 281:1309–1312, 1998; Reed, et al., *Cancer J. Sci. Am.* 4 Suppl. 1:S8–14, 1998). Mitochondria release apoptogenic factors during apoptosis such as cytochrome c apoptosis-inducing factor (AIF), and SMAC/DIABLO (Green, 2000). cytochrome c released from mitochondria into the cytosol space triggers Apaf-1-dependent caspase activation leading cells to death (Green, *Cell* 102:1–4, 2000; Zou, et al., *Cell* 90:405–413, 1997). Pro-apoptotic Bcl-2 family proteins such as Bax promote cytochrome c release from mitochondria (Jurgensmeier, et al., *Proc. Natl. Acad. Sci. USA* 95:4997–5002, 1998). On the other hand, anti-apoptotic Bcl-2 family proteins such as Bcl-2 suppress cytochrome c release from mitochondria, thereby protecting cells from apoptotic signals triggered by several stimuli (Kluck, et al., *Science* 275:1132–1136, 1997; Yang, et al., *Science* 275:1129–1132, 1997). The relative ratios of these various pro- and anti-apoptotic members of the Bcl-2 family have been known to determine the sensitivity of cells to diverse apoptotic stimuli (Oltvai and Korsmeyer, *Cell* 79:189–192, 1994) including chemotherapeutic drugs and radiation, growth factor deprivation, loss of cell attachment to extracellular matrix, hypoxia (a common occurrence in the centers of large tumors), and lysis by cytotoxic T-cells (Adams and Cory, supra, 1998; Green and Reed, supra, 1998; Gross, et al., supra, 1999; Reed, *Semin. Hematol.* 34:9–19, 1997).

Among pro-apoptotic Bcl-2 family members, Bax and Bak play a key role for apoptosis induction. The double knock out of these genes in mice resulted in the resistance of the cells to several cell death stimuli known to trigger mitochondria-dependent apoptosis, such as UV-irradiation, staurosporin (pan-kinase inhibitor), and some anti-cancer drugs (Wei, et al., *Science* 292:727–730, 2001). Bax normally resides in the cytosol in a quiescent state. Upon receipt of apoptotic stimuli, Bax translocates into mitochondria (Wolter, et al., *J. Cell. Biol.* 139:1281–1292, 1997), and promotes cytochrome c release, possibly by forming a pore in the mitochondrial outer membrane (Korsmeyer, et al., *Cell Death Differ.* 7:1166–1173, 2000; Saito, et al., *Nat. Cell Biol.* 2:553–555, 2000). On the other hand, anti-apoptotic family proteins such as Bcl-2 and Bcl-XL reside in the mitochondrial membrane and antagonize the cytotoxic activity of Bax moved from the cytosol (Adams and Cory, supra, 1998; Green and Reed, supra, 1998; Reed, et al., supra, 1998). Mitochondrial translocation of Bax is one of the critical steps for the induction of apoptosis, however the mechanism is not yet fully understood.

Translocation of Bax from the cytosol to the mitochondria is caspase-independent, since caspase-inhibitor pretreatment does not interfere with this process (Goping, et al., *J. Cell Biol.* 143:207–215, 1998). C-terminus hydrophobic residues forming the ninth (α-helix of Bax are reported to be involved in the translocation of Bax to the mitochondrial membrane (Suzuki, et al., *Cell* 103:645–654, 2000). On the other hand, the N-terminus of Bax functions as a cytosol retention domain, since the deletion of this region allowed Bax to accumulate in the mitochondrial membrane in the absence of apoptotic stimuli (Goping, et al., supra, 1998). The previous observations suggest that unidentified cytosolic factor(s) interact with the N-terminus of Bax to inhibit its translocation to mitochondria in the absence of an apoptotic stimulus.

U.S. application Ser. No. 10/247,045 describes the suppression of BAX by Ku-70, a factor that binds the N-terminus of Bax and prevents its mitochondrial translocation. The present invention involves the development of a membrane permeable peptide that inhibits Bax-mediated apoptosis.

BRIEF SUMMARY OF THE INVENTION

In one embodiment, the present invention is a method of protecting cells from cell death comprising the step of supplying to the cell an effective amount of a composition comprising a Bax-inhibiting peptide. In one specific embodiment, the peptide comprises a peptide selected from the group consisting of the VPMLK (SEQ ID NO: 1), PMLKE (SEQ ID NO: 2) and PMLK (SEQ ID NO: 3).

In another embodiment, the peptide is of the following formula: $X^1PX^2LX^3X^4$ (SEQ ID NO: 4), wherein $X^1$ is selected from amino acids with non-polar side chain; $X^2$ is selected from amino acids with non-polar side chain; $X^3$ is selected from amino acids with charged polar side chain; $X^4$ is selected from amino acids with charged polar side chain; and either $X^1$ or $X^4$ may be absent, although both may not be absent.

In one preferred embodiment, the Bax-inhibiting peptide is administered to a patient.

In one embodiment, the invention is a preparation of one of the compositions comprising peptides described above.

In another embodiment, the invention is a method of protecting cells from cell death comprising the steps of: (a) designing a composition comprising a peptide or chemical that mimics the Bax-suppressing function of VPMLK (SEQ ID NO: 1), PMLKE (SEQ ID NO: 2) or PMLK (SEQ ID NO: 3), and (b) supplying cells with an effective amount of the composition.

In another embodiment, the invention is a pharmaceutical composition comprising a Bax-inhibiting peptide and a pharmaceutical carrier, wherein the peptide is of the following formula: $X^1PX^2LX^3X^4$ (SEQ ID NO: 4) wherein $X^1$ is selected for amino acids with non-polar side chain; $X^2$ selected for amino acids with non-polar side chain; $X^3$ is selected for amino acids with charged polar side chain; $X^4$ selected for amino acids with charged polar side chain; and either $X^1$ or $X^4$ may be absent, but both may not be absent.

The invention is also a method of preserving cells and organs for transfusions or transplantation comprising storing the cells or organs in an effective amount above-identified peptide.

The invention is also a method of regeneration of damaged cells, comprising storing the cells in an effective amount of the peptide.

The invention is also a method of improving transfection efficiency of genes or proteins into cells, comprising storing the cells in an effective amount of the peptide.

BRIEF DESCRIPTION OF THE SEVERAL VIEWS OF THE DRAWINGS

FIGS. 2A and 2B: HeLa cells ($10^6$ cells) were preincubated with 200 uM negative control (NC) peptide for 1 hour or V5 peptide for the indicated periods, and then treated with 200 nM STS (A) or 1200 J/$m^2$ UVC-irradiation (B). After 24 hours of apoptotic treatment, apoptotic cells were counted as described in FIG. 1. FIG. 2C: HeLa cells were preincubated with V5 peptide and/or z-VAD-fmk (Calbiochem), a pan-caspase inhibitor, at the indicated concentrations for 1 hour and then exposed to 1200 J/$m^2$ of UVC-irradiation. The number of apoptotic cells was determined one day after UVC-irradiation as described in FIG. 1. FIGS. 2D–L: U87-MG glioma (D–F), MCF-7 breast cancer (G–I), and LNCaP prostate cancer cells (J–L) were preincubated with 200 uM negative control (NC) peptide or V5 peptide at the indicated concentrations, and then treated with 20 uM etoposide (D, G, J), 20 uM cisplatin (E, H, K), or 1 uM doxorubicin (F, I, L). Apoptotic cells were analyzed at the indicated periods following the treatment with anti-cancer drugs as described in FIG. 1.

FIGS. 3A–D: Du145 cells ($10^6$ cells) were transfected with 1.0 ug pcDNA3-control vector (Control) or 0.125 ug pcDNA3-Bax (Bax) together with 0.5 ug pEGFP for the marking of transfected cells. One day following transfection, cells were incubated with 200 uM negative control (NC) peptide, V5 peptide, or P5 peptide for 1 hour, and then treated with 200 nM STS (A, B) or 1200 J/$m^2$ of UVC-irradiation (C, D). After 24 hours of apoptotic treatment, apoptotic cells were counted as described in FIG. 1. BIP does not require Ku70 to suppress apoptosis (E, F). Mouse embryonic fibroblasts (MEF) derived from Ku70-deficient (Ku70–/–) mice were treated with 200 nM STS (E) or 1200 J/$m^2$ UVC-irradiation (F) in the presence of 200 uM negative control (NC) peptide or V5 peptide. Apoptotic cells were analyzed at the indicated periods following the treatment with STS or UVC-irradiation as described in FIG. 1.

FIG. 4A: One day following UVC-irradiation or STS-treatment in the absence (UV and STS) or presence of 200 uM negative control (NC) peptide (UV+NC and STS+NC) or V5 peptide (UV+V5 and STS+V5), subcellular fractionation of HeLa cells ($10^6$ cells) was performed. FoF1 ATP synthase subunit α (F1α) was used to mark the mitochondrial fraction. HM stands for "Heavy Membrane" fraction containing mitochondria. FIG. 4C: cytochrome c release from mitochondria is inhibited by BIP, but not z-VAD-fmk. HeLa cells ($10^6$ cells) were treated with 200 nM STS in the presence or absence of 200 uM negative control (NC) peptide, V5 peptide, or z-VAD-fmk for 24 hours. Cytochrome c released from mitochondria into cytosol was analyzed by subcellular fractionation followed by Western blot analysis of cytochrome c (cyt c) as well as mitochondrial FoF1-ATP-synthase subunit F1α (F1α) as described in Methods. FIG. 4D: BIP suppresses STS-induced Caspase activation as well as z-VAD-fmk. HeLa cells ($10^6$ cells) were treated with 200 nM STS in the presence or absence of 200 uM negative control (NC) peptide, V5 peptide, or z-VAD-fmk for 24 hours. Caspase activity was assessed as described in Methods. FIG. 4F: Scatchard analysis of the interaction of BIP and Bax. Scatchard analysis of the binding of FITC-labeled BIP (VPMLK; SEQ ID NO: 1) and endogenous Bax in Ku70-deficient MEFs was performed as described in Methods. The dissociation constant (Kd) was estimated to be 1.3 uM (1/Ka) for this interaction. No significant binding of FITC-BIP to the cellular components was detected in Bax-immunodepleted cell lysates.

FIGS. 6A–D: HEK293T cells ($10^7$ cells) lysed in CHAPS buffer were incubated with 200 uM negative control (NC) peptide or (A) VPMLK (V5, SEQ ID NO: 1), (B) PMLKE (P5, SEQ ID NO: 2), (C) PMLK (P4, SEQ ID NO: 3), and (D) MLKE (M4, SEQ ID NO: 6) at the indicated concentrations for 1 hour. Immunoprecipitation was performed with anti-Ku70 monoclonal antibody or anti-Bax polyclonal antibody using CHAPS buffer as described in Methods. Mouse IgG and pre-immune rabbit serum (NRS) were used as negative controls.

FIG. 7 demonstrates optimization of Bax-plasmid transfection into Du145 cells.

DETAILED DESCRIPTION OF THE INVENTION

In General

Figure 1A:
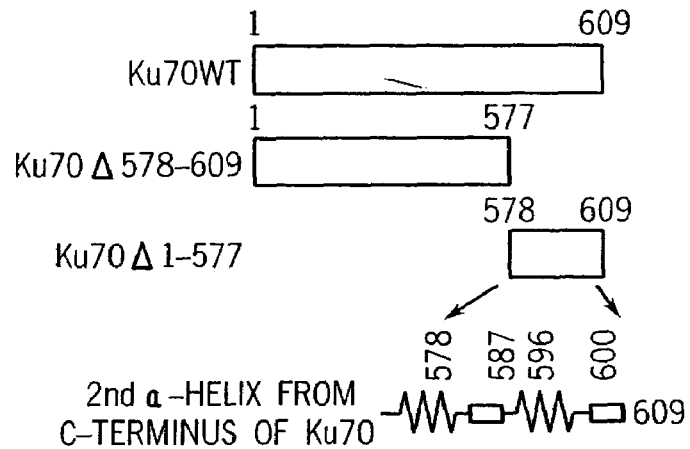
FIG. 1A: scheme of Ku70 full-length (Ku70 wt), $Ku70_{1-577}$ (Ku70Δ578–609), or $Ku70_{578-609}$ (Ku70Δ1–577).

Bax is a pro-apoptotic member of Bcl-2 family of proteins and plays a key role in mitochondria-dependent apoptosis. Bax resides in the cytosol as a quiescent protein, and translocates into mitochondria upon the receipt of apoptotic stimuli. Ku70 has been known to be a 70 kDa subunit of Ku-complex that plays an important role in DNA double strand break repair in the nucleus. We reported that Ku70 interacts with pro-apoptotic protein Bax in the cytosol and prevents the mitochondrial translocation of Bax, and thus Ku70 suppresses Bax-mediated apoptosis. (See U.S. Ser. No. 10/247,045)

In the present invention, we disclose the development of a new membrane permeable peptide (Bax-Inhibiting Peptide; BIP) that inhibits Bax-mediated apoptosis and appears to mimic Ku70 in its interaction with the Bax molecule. In one embodiment, BIP is comprised of five amino acids designed from Bax-binding domain of Ku70 and suppresses the mitochondrial translocation of Bax. A BIP inhibits Bax-mediated apoptosis induced by saturosporin, UVC-irradiation, and anticancer drugs in several types of cells as disclosed below in the Examples.

By testing several deletion mutants of the Ku70 protein, I have identified the Bax-binding domain in Ku70. The domain comprises 6 amino acids (VPMLKE, SEQ ID NO: 7). This peptide (Ku70 Peptide V6) inhibits the interaction of Ku70 and Bax at the concentration of 20–80 μM in lysates prepared from human cultured cells (HeLa cells and human kidney epithelial 293 cells). Negative control experiments using the scrambled sequence of these 6 amino acids and the immediate next six amino acid sequence of Ku70 (Ku70 573–578 peptide, termed "Ku70 Peptide NC") did not affect the interaction of Ku70 and Bax, indicating the specificity of Ku70 Peptide V6 activity. Delivering the Ku70 peptide V6 into the cells also inhibits mitochondrial translocation of Bax in the cells treated by several apoptotic stresses such as UV-irradiation and staurosporin-treatment.

Ku70 Peptide V6 also suppressed cell death of human cultured cells (HeLa cells) treated by UV-irradiation and staurosporin. VPMLK (V5; SEQ ID NO: 1) and PMLKE (P5; SEQ ID NO: 2), deletion mutations, also showed anti-cell death activity. Importantly, V5 and P5 are membrane permeable and do not require a cell delivery system such as liposomes as in the case of V6. In one embodiment, the present invention is a Bax-inhibiting peptide, preferably VPMLKE (SEQ ID NO: 7), VPMLK (SEQ ID NO: 1), and PMLKE (SEQ ID NO: 2) (V6, V5, and P5, respectively), that can protect cells from death and use of the peptide for this purpose. The sequences of these peptides were designed from the Bax-binding domain in the Ku70 protein (amino acid 578–583).

The original 6 amino acid peptide V6 (VPMLKE; SEQ ID NO: 7) and its variants, including shorter amino acid peptides (e.g. VPMLK (V5; SEQ ID NO: 1), PMLKE (P5; SEQ ID NO: 2)) and modified peptides (e.g. modified for better membrane permeablization or longer stability) are also Box-inhibiting peptides, may be also suitable drugs to protect cells and tissues from pathological damage and are included within the present invention.

The present invention also includes peptides (preferably 6–3 residues) and chemicals (natural and synthetic compounds) designed to mimic the described Ku70 peptides. By "mimic," I mean that the peptide has at least 90% of the Bax-suppressing function of V5 and P5, as measured by the method of the Examples below. If a peptide or compound suppresses apoptosis by blocking the mitochondrial translocation of Bax, these chemicals or peptides successfully "mimic" Ku70 peptide.

Suitable methods for creating mimics can be found at: WO00/21980, EP1077218A2, WO01/60844, WO01/14412, WO01/55091, WO01/46197, WO02/20033, WO02/20034, WO02/20557, incorporated by reference. The following articles, incorporated by reference, would also guide one to make a Ku70 mimic: P. C. A. Kam, "Platelet glycoprotein IIb/IIIa antagonists," *Anesthesiology* 96:1237–1249, 2002; S. Mousa, "Antiplatelet therapies: From aspirin to GPIIb/IIIa inhibitors and beyond," *Drug Discovery Today* 4:552–561, 1999; R. S. McDowell, et al., "From peptide to non-peptide. 2. The de novo design of potent, non-peptidal inhibitors of platelet aggregation based on a benzodiazepine scaffold," *J. Am. Chem. Soc.* 116:5077–5083, 1994; and B. K. Blackburn, et al., "From peptide to non-peptide. 3. Atropisomeric GPIIb/IIIa antagonists containing the 3,4-dihydro-1,4-benzodiazepine-2,5-dione nucleus," *J. Medicinal Chem.* 40:717–729, 1997.

Peptides with slight modifications (e.g., substitution of similar charged amino acids or addition of 1, 2 or 3 innocuous amino acids at either end or by the addition of an innocuous entity or moiety) to the peptide sequences described herein are envisioned to be suitable BIPs. By "innocuous" I mean amino acid(s) or entities that do not substantially reduce the Bax-inhibiting activity of the core peptide sequence PMLK (SEQ ID NO: 3). Therefore, a composition comprising a Bax-inhibiting peptide of the present invention includes a peptide described herein (e.g., PMLK (SEQ ID NO: 3), PMLKE (SEQ ID NO: 2), VPMLK (SEQ ID NO: 1), VPMLKE (SEQ ID NO: 7) and the formula below) with additions of 1, 2 or 3 innocuous amino acids at either end, innocuous amino acid substitutions, addition of innocuous moieties or entities, and mimics of these peptides.

Peptide drug delivery and therapeutic administration is limited by permeability and selectivity problems involving the cell membrane (Morris, et al., *Nat. Biotechnol.* 19(12): 1173–1176, 2001). Strategies to deliver peptides and proteins into cells may solve these problems. Many small protein domains, called protein transduction domains (PTD's), have been shown to cross biological membranes and act independently from transporters or specific receptors to promote delivery of peptides and proteins into cells. The work of Hawiger (Hawiger, *Curr. Opin. Chem. Biol.* 3(1): 88–94, 1999) is one example of how we envision this technique involving peptide modification could be applied to create a composition comprising BIP that consists of adding a PTD domain at position $X^1$ or $X^4$ to aid in either the transport or BIP to specific target cells or to aid the stability of the molecule.

The present invention also includes peptides in which sequences described above are repeated multiple times.

Because the amino acid sequences VPMLK (SEQ ID NO: 1) and PMLKE (SEQ ID NO: 2) are equally effective to suppress Bax, the amino acid sequence PMLK (SEQ ID NO: 3) is considered to be the core structure for BIP's biological activity. Indeed, PMLK (SEQ ID NO: 4) is sufficient to bind Bax in vitro. However, PMLK (SEQ ID NO: 4) is not biologically active because these four amino acids are not retained in the cell. Addition of V before P, or E after K of PMLK (SEQ ID NO: 4) causes the peptide(s) to be effectively retained inside the cells. Therefore, these peptides (VPMLK; SEQ ID NO: 1 or PMLKE; SEQ ID NO: 2) express anti-Bax activity in cells and are Bax-inhibiting peptides.

I assume that the addition of the fifth amino acid to PMLK (SEQ ID NO: 3) is required for either solubility of BIP in the cytosol or protection of the export of BIP through cell membrane. Therefore, other amino acids which retain similar polarity are expected to be suitable substitutes for V and E.

In PMLK (SEQ ID NO: 3), P and L seem to be required for effectiveness. Because P has very unique structure among amino acids, and substitution of L with I (L and I are non-polar amino acids) diminish BIP's biological activity (described in Nature Cell Biology BIP paper).

In PMLK (SEQ ID NO: 3), M and K may be interchangeable with other amino acids in the same group with similar polarity.

Based on the above logic, we describe the formula of the future modification of a preferred embodiment of the BIP as comprising the peptide $X^1PX^2LX^3X^4$ (SEQ ID NO: 4), wherein $X^1$=Amino acids with non-polar side chain, such as Glycine (G), Alanine (A), Valine (V), Leucine (L), Isoleucine (I), Methionine (M), Proline (P), Phenylalanine (F), Tryptophan (W).

$X^2$=Amino acids with non-polar side chain, such as Glycine (G), Alanine (A), Valine (V), Leucine (L), Isoleucine (I), Methionine (M), Proline (P), Phenylalanine (F), Tryptophan (W).

$X^3$=Amino acids with charged polar side chain, such as Lysine (K), Arginine (R), Histidine (H), Aspartic acid (D), Glutamic acid (E), and $X^4$=Amino acids with charged polar side chain, such as Lysine (K), Arginine (R), Histidine (H), Aspartic acid (D), Glutamic acid (E).

Either $X^1$ or $X^4$ may be absent.

I envision that 1, 2 or 3 innocuous amino acids or innocuous entities or moieties may be added at either end of the peptide or to the peptide itself without significantly reducing its Bax-inhibiting activity. These are suitable compositions comprising a Bax-inhibiting peptide.

In a preferred embodiment, the present invention is a pharmaceutical preparation comprising a BIP and a pharmaceutical carrier. The potential application of the drugs or pharmaceutical preparation based on this discovery are drugs to protect the death of cells and tissues damaged by stroke, heart attack, ischemia, degenerative diseases (neuron and muscle, e.g. Alzheimer disease, Parkinson's disease, cardiomyocyte degeneration, etc), infection by parasitic organisms (virus, bacteria, yeast, or protozoa, etc), side-effects of other drugs (e.g. anti-cancer drugs), UV/X-ray irradiation, and several other pathological conditions triggering cell death signals. Other potential applications include supporting the regeneration of damaged cells, including neuron and muscle cells; improving transfection efficiency of genes and proteins into cells, and preserving cells and organs for transfusion or transplantation.

The following references describe the Bax protein playing a key role in various diseases: Injury-induced neuron death—Deckwerth, et al. *Neuron.* 17:401–411, 1996; Martin, et al., *J. Comp. Neurol.* 433:299–311, 2001; Kirkland, et al., *J. Neurosci.* 22:6480–90, 2002; Alzheimer disease—MacGibbon, et al., *Brain Res.* 750:223–234, 1997; Selznick, et al., *J. Neuropathol. Exp. Neurol.* 59:271–279, 2000; Cao, et al., *J. Cereb. Blood Flow Metab.* 21 :321–333, 2001; Zhang, et al., *J. Cell Biol.* 156:519–529, 2002; Ischemia-induced cell damage—Kaneda, et al., *Brain Res.* 815:11–20, 1999; Gibson, et al., *Mol. Med.* 7:644–655, 2001; HIV (AIDS) and Bax: Castedo, et al., *J. Exp. Med.* 194:1097–1110, 2001; Drug-induced neuron death—Dargusch, et al., *J. Neurochem.* 76:295–301, 2001; Parkinson's disease—Ploix and Spier, *Trends Neurosci.* 24:255, 2001; Huntington's disease—Antonawich, et al., *Brain Res. Bull.* 57:647–649, 2002.

One would most likely administer the BIP orally, by intravenous infusion, intramuscular or subcutaneous injection, or by inhalation or intracranial injection.

EXAMPLES

Figure 1C:
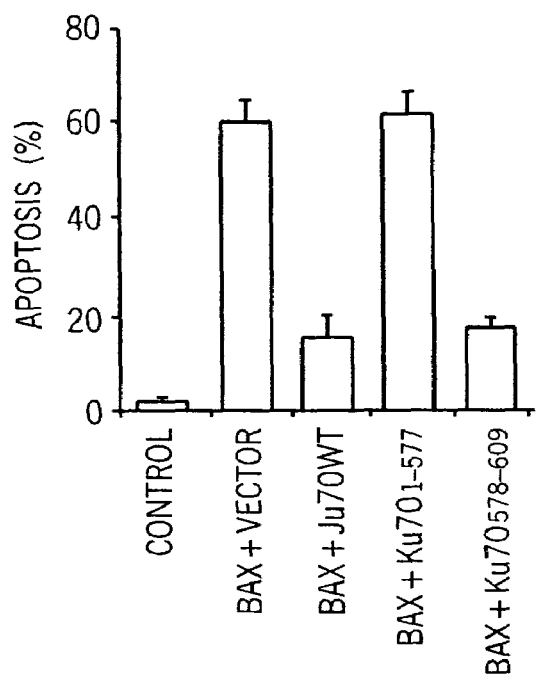
FIG. 1C: HEK293T cells were transfected with 1.0 ug of pCMV-2B-control vector (Control) or pcDNA3-Bax (Bax) together with 2.0 ug of pCMV-2B-Ku70 wt (Ku70 wt), pCMV-2B-$Ku70_{1-577}$ ($Ku70_{1-577}$), or pCMV-2B-$Ku70_{578-609}$ ($Ku70_{578-609}$). All the cells were also co-transfected with 0.5 ug pEGFP for the marking of transfected cells. Apoptosis in the transfected cells was analyzed 24 hours following transfection with Hoechst dye staining of the nucleus as described in Methods.

Anti-Bax activity of new peptides designed from Ku70. We found that the C-terminal 74 amino acids of Ku70 are sufficient to bind Bax and to inhibit Bax-mediated apoptosis in several types of cells. Recent structural analysis of Ku70 revealed that the 74 amino acid C-terminal portion is comprised of three α-helices and four flexible loop domains (FIG. 1A). Further analysis of a series of deletion mutants of Ku70 revealed that the C-terminal 32 amino acids are sufficient for the inhibition of Bax-induced apoptosis in HEK293T cells (FIG. 1A, C). Flag-tagged Ku70 mutant expressing the amino acids 578–609 ($Ku70_{578-609}$) of Ku70 binds endogenous Bax, whereas the Ku70 mutant deleted with these amino acids (Ku70$_{1-577}$) did not. Ku70$_{578-609}$, but not Ku70$_{1-577}$, suppressed Bax-induced apoptosis in HEK293T cells (FIG. 1C). These results suggest that the Bax-inhibiting domain of Ku70 localizes in the amino acids 578–609 of Ku70.

Figure 1D:
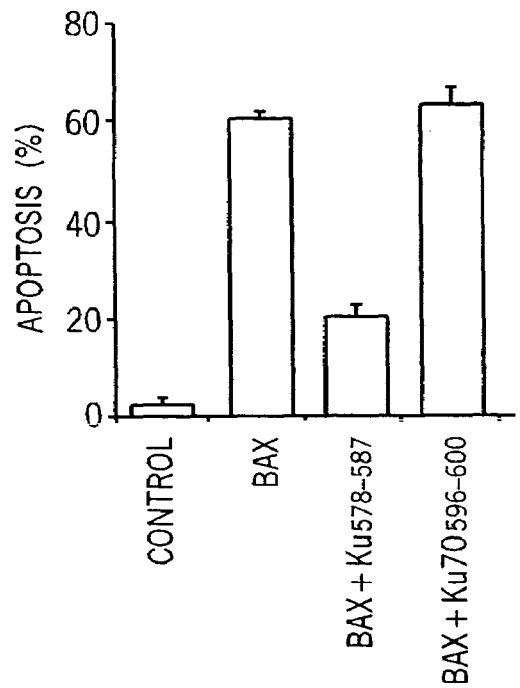
FIG. 1D: HEK293T cells were incubated with 200 uM peptide composed of $Ku70_{578-587}$ or $Ku70_{596-600}$ for 4 hours using BioPorter reagent, and then transfected with 1.0 ug of pCDNA3-control vector (Control) or pcDNA3-Bax (Bax). The number of apoptotic cells was determined as described in FIG. 1C.
Figure 1B:
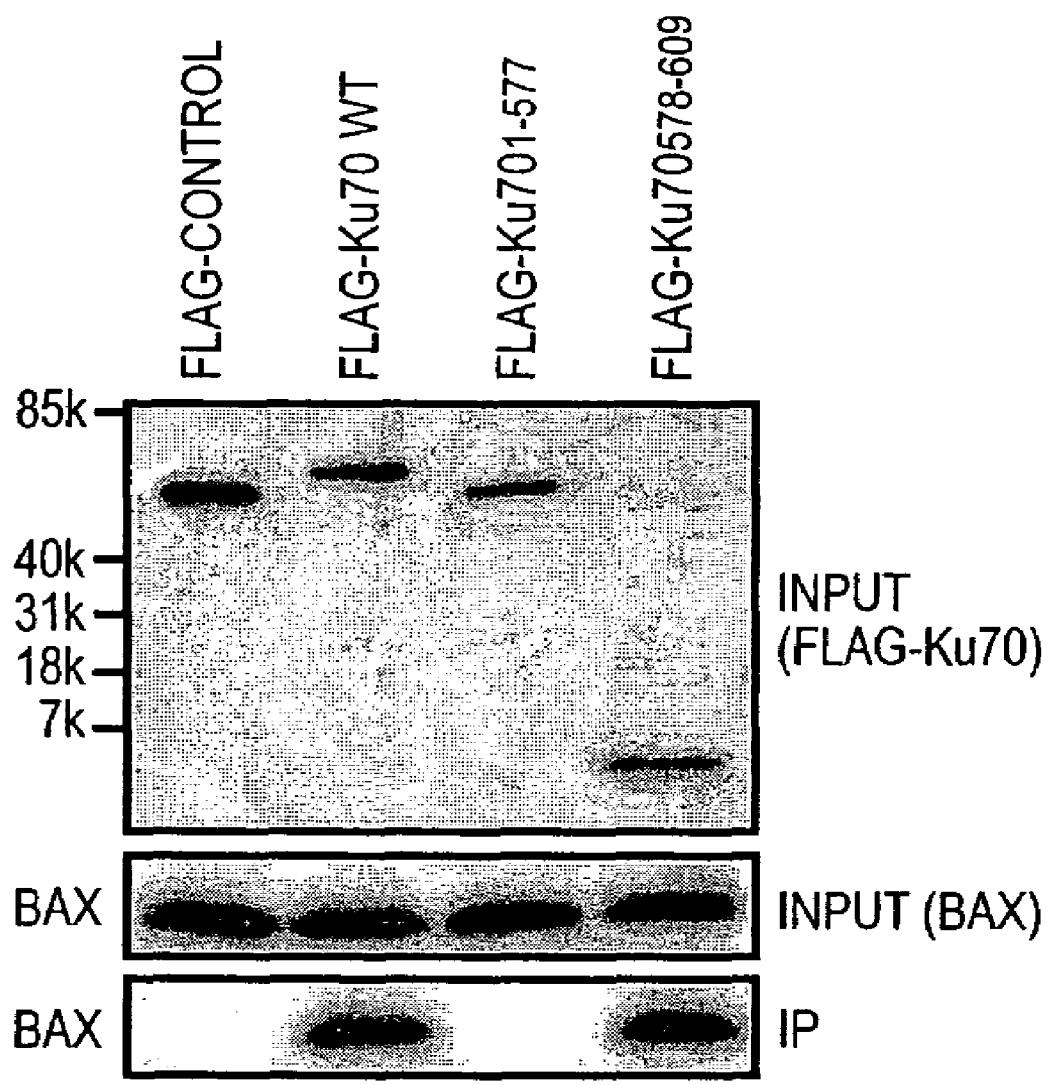
FIG. 1 illustrates that new peptides designed from Ku70 show anti-Bax activity.
FIG. 1E: HEK293T cells ($10^6$ cells) were incubated with 200 uM IPMIK (negative control peptide) or VPMLK (V5) and PMLKE (P5) peptides at the indicated concentrations for 1 hour and then incubated cells were transfected with 1.0 ug of pcDNA3-Bax. Also, unincubated cells were transfected with 1.0 ug of pcDNA3-Bax in the presence or absence of 200 uM z-VAD-fmk. The number of apoptotic cells was determined as described in FIG. 1C.
FIG. 1F: Summary of the anti-Bax activity and sequence of all peptides used.

There are two α-helices in these 32 amino acids according to the previous reports (FIG. 1A). Synthetic peptides corresponding to these two α-helices were made and their activities to suppress Bax-induced apoptosis were tested (FIG. 1D). Since these peptides are not membrane permeable, FITC-labeled peptides were delivered into the cells by liposome (BioPorter) and the presence of the peptides in the cells were confirmed by FITC fluorescence (not shown). The peptide of 578–587, but not 596–600, inhibited Bax-induced apoptosis, suggesting that the Bax-inhibiting domain is the 2$^{nd}$ α-helix from the C-terminus of Ku70 (FIG. 1D).

Figures 1E, 1F:
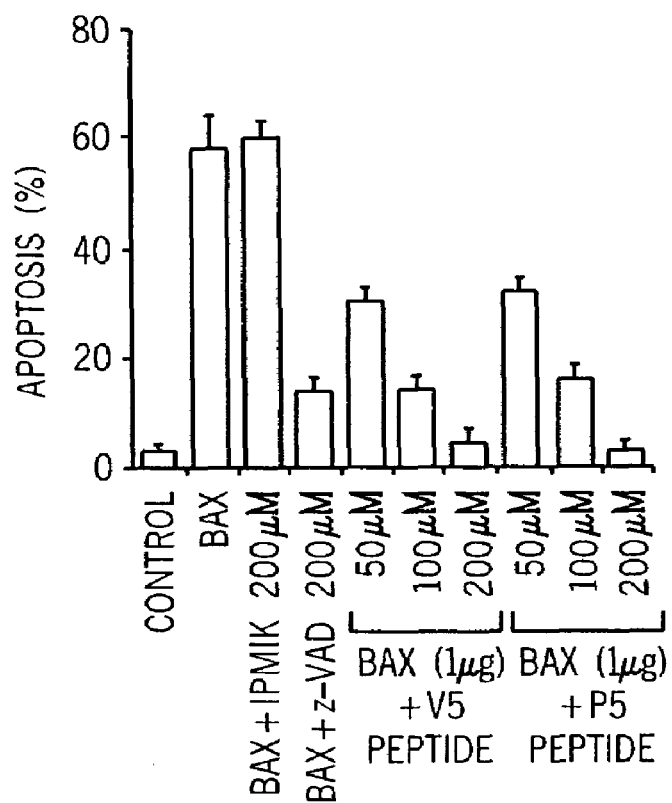
Figure 8:
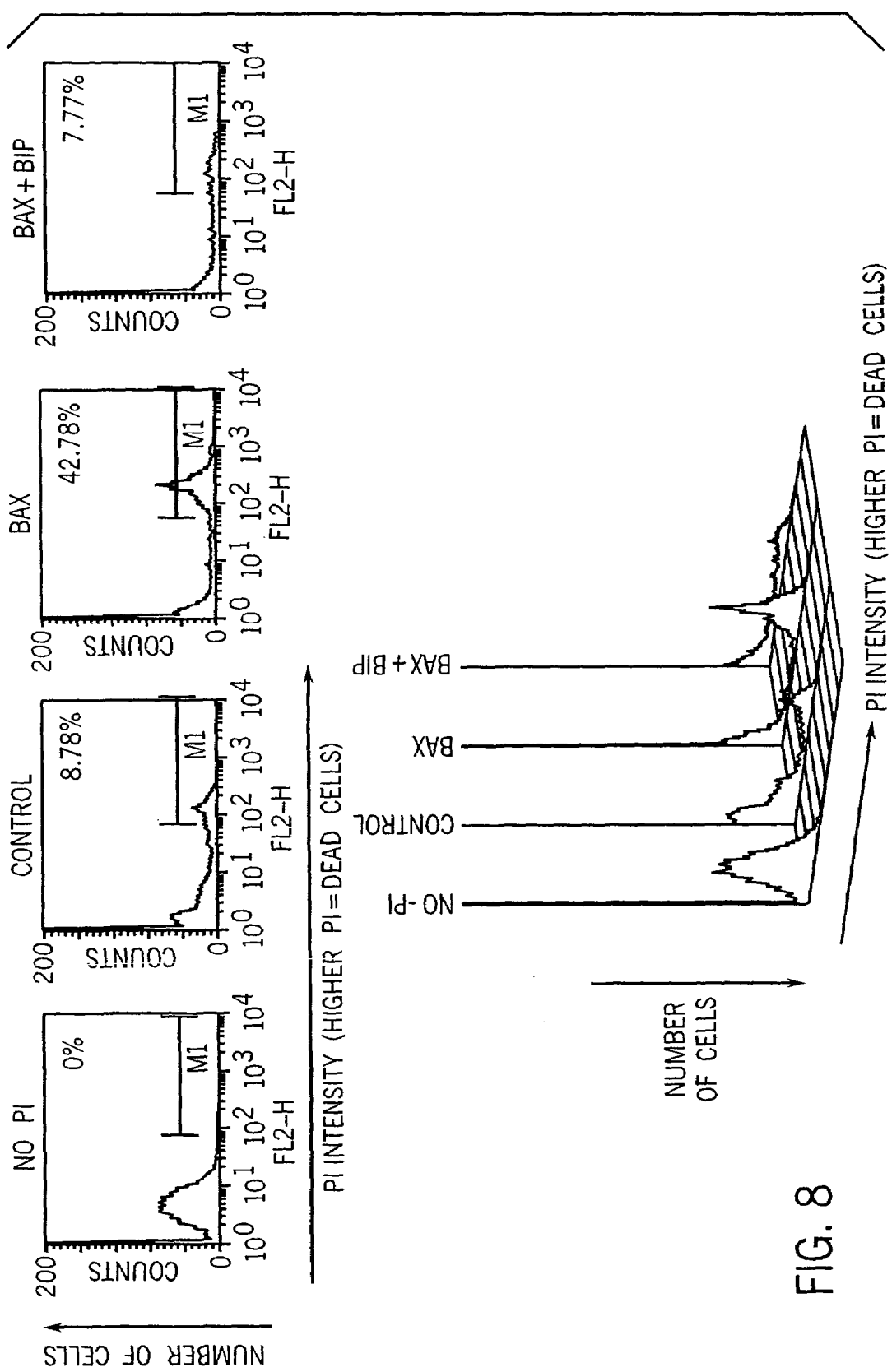
FIG. 8 demonstrates that BIP inhibits Bax-mediated apoptosis as measured by propidium iodide (PI) exclusion. HEK293T cells ($10^6$ cells) were transfected with 1.0 ug of pcDNA3 (Control) or pcDNA3-Bax (Bax) in the absence or presence (Bax+BIP) of 200 uM V5 peptide. HBSS (Hanks' balanced salt solution)-washed live cells were incubated with 1 ug/ml of PI (Sigma) for 10 minutes at 4° C. in the dark. Flow cytometry was performed using a Becton Dickinson FACScan instrument. The percentage shown in the figure indicates the percentage of "dead" cells (PI-positive).

Further analysis of the peptides designed from Bax-inhibiting domain in Ku70 revealed that the six amino acids (VPMLKE; SEQ ID NO: 7; V6-peptide) in the Bax-inhibiting domain (amino acids 578–587) of Ku70 are sufficient to suppress Bax-mediated apoptosis (Bax-overexpression-, staurosporin (STS)-, or UVC-induced apoptosis) (data not shown). However, V6-peptide is not membrane permeable and liposome-mediated delivery of the peptide is required to suppress Bax-mediated apoptosis. Interestingly, the deletion of one amino acid from VPMLKE (SEQ ID NO: 7) at either the N-terminus or the C-terminus makes these peptides membrane-permeable, and did not abrogate Bax-inhibiting activity (FIGS. 1E, F). As shown in FIGS. 1E, 1F and FIG. 8, the five amino acids peptides VPMLK (V5; SEQ ID NO: 1) and PMLKE (P5; SEQ ID NO: 2) are equally effective in suppressing apoptosis induced by Bax. Since V5 or P5 is membrane permeable, the addition of these peptides into the culture medium is sufficient to block Bax-mediated apoptosis. However, further deletion of one amino acid resulted in the abrogation of Bax-inhibiting activity (FIG. 1F). When the amino acids V and L in V5-peptide (VPMLK; SEQ ID NO: 1) were changed with another non-polar amino acid I, the peptide (IPMIK; SEQ ID NO: 5) lost its activity to suppress apoptosis (FIGS. 1E, F). The mutant peptide IPMIK (SEQ ID NO: 5) is used as negative control (NC) peptide in the following experiments.

Figure 2A:
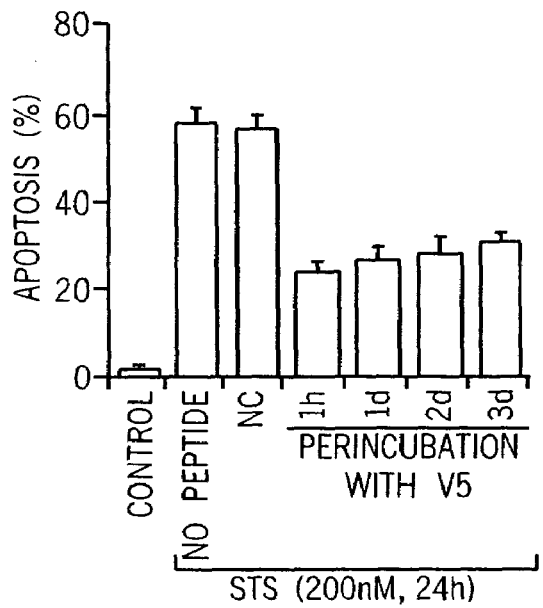
FIGS. 2A–L are graphs demonstrating inhibitory effects of Bax-inhibiting peptides (BIP) against various apoptotic stimuli.
Figure 2B:
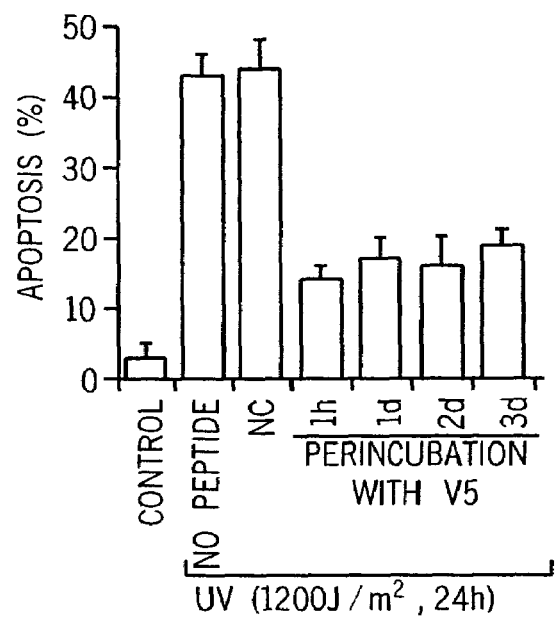
Figure 2C:
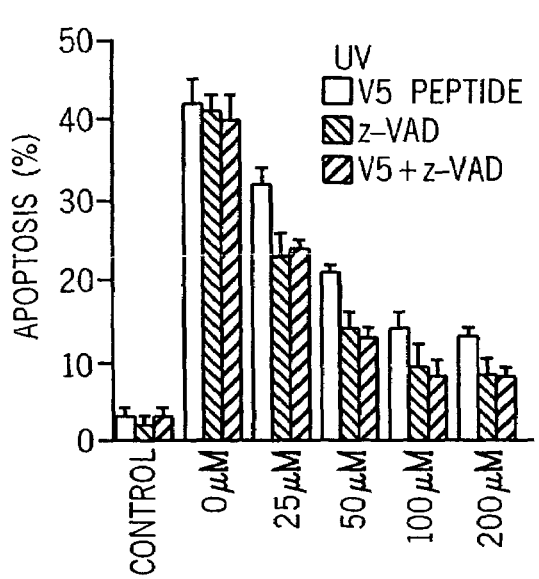
Figure 2D:
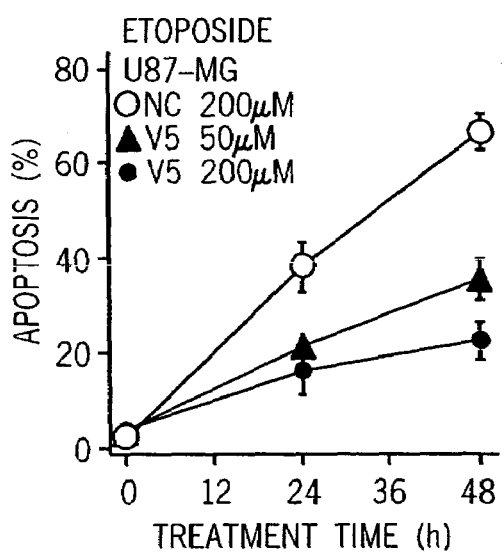
Figure 2E:
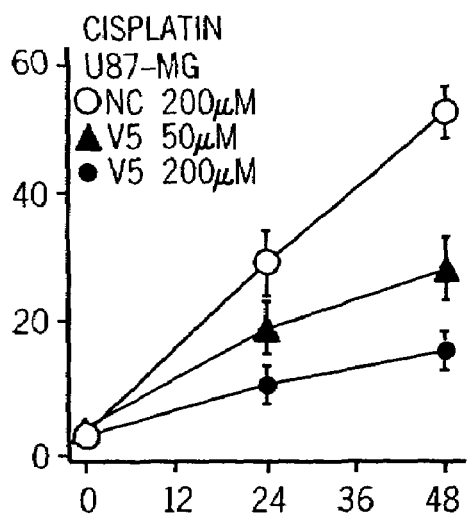
Figure 2F:
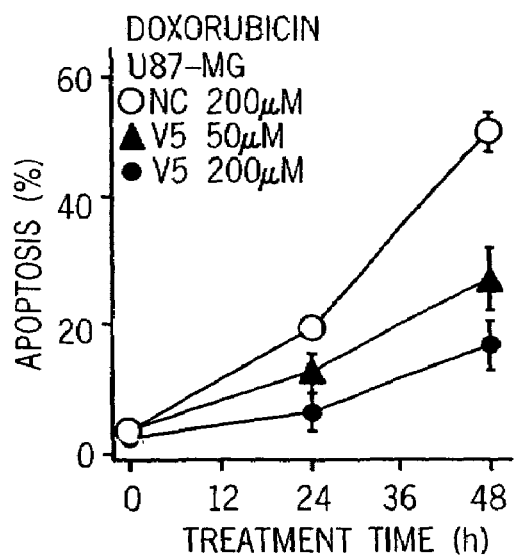
Figure 2G:
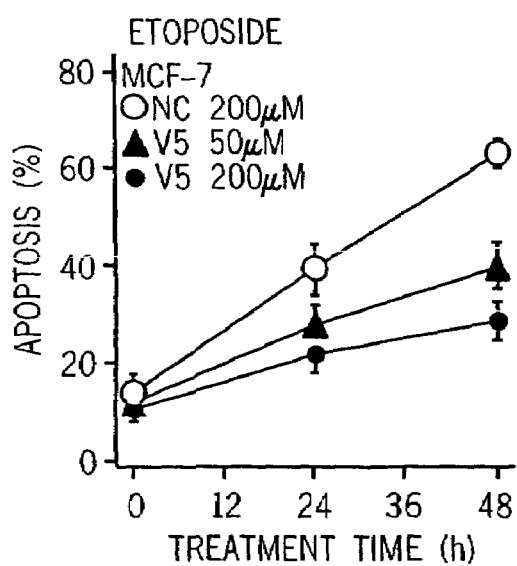
Figure 2H:
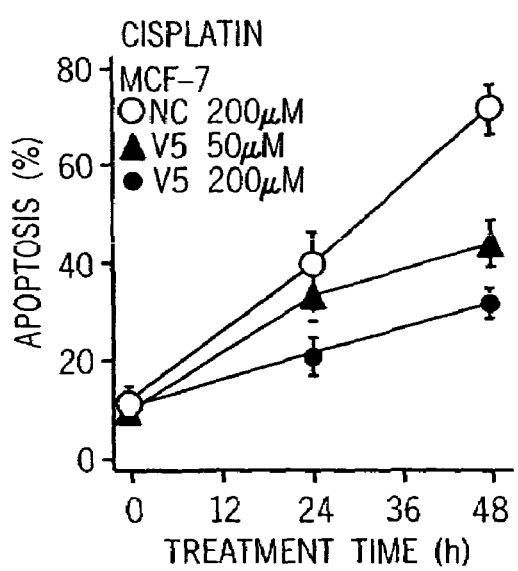
Figure 2I:
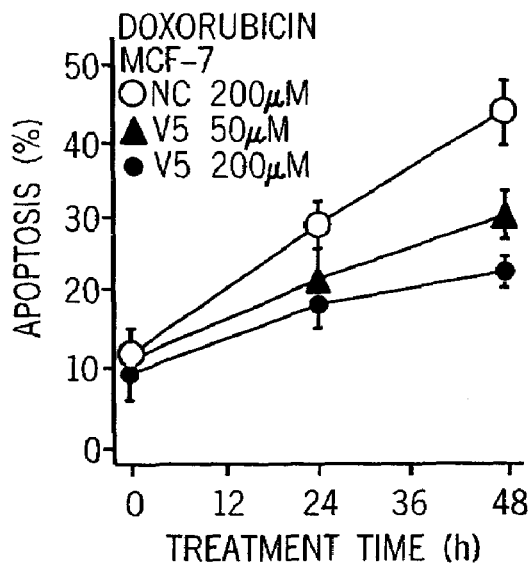
Figure 2J:
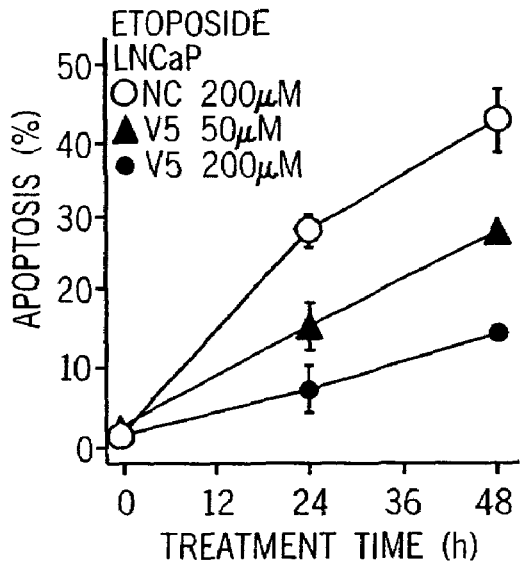
Figure 2K:
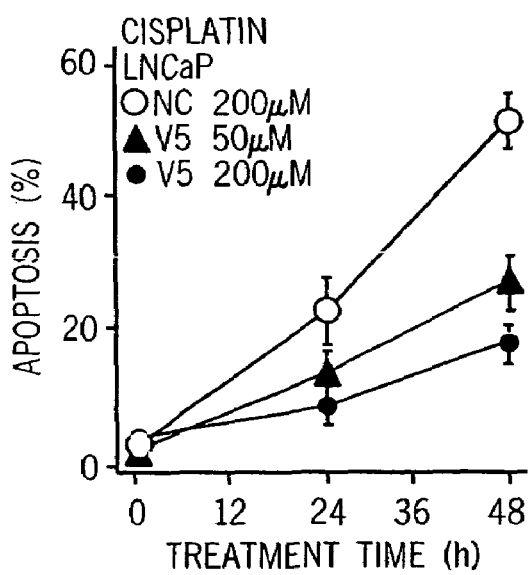
Figure 2L:
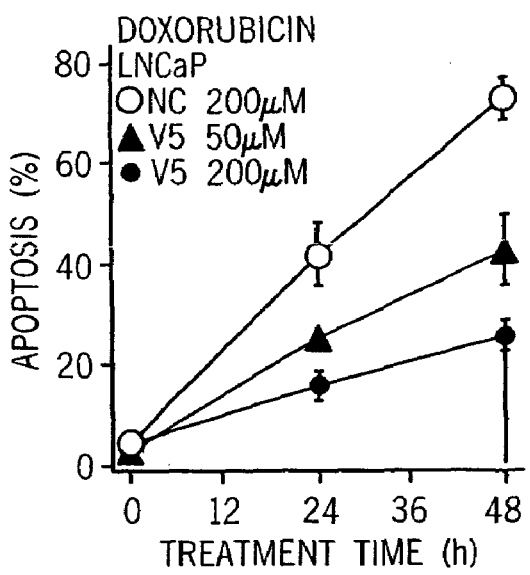
Figure 3A:
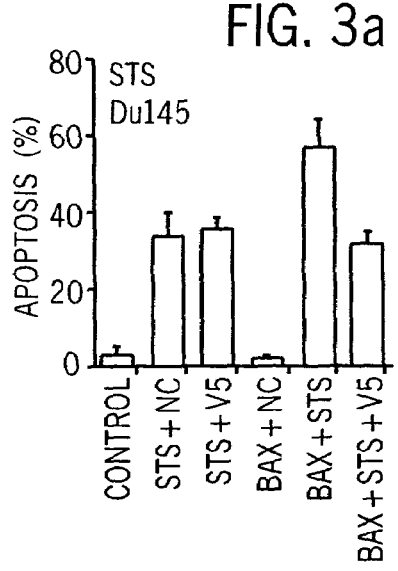
FIGS. 3A–F are a set of graphs illustrating the effects of BIP in Bax- or Ku70-deficient cells.
Figure 3B:
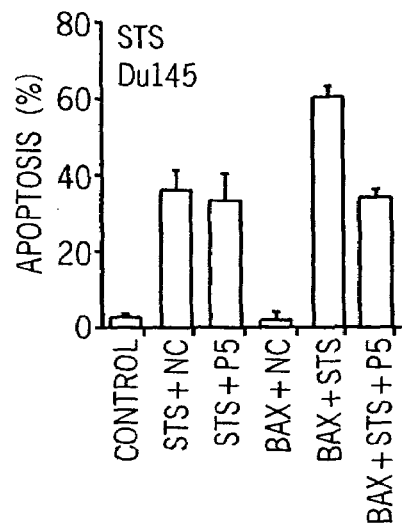
Figure 3C:
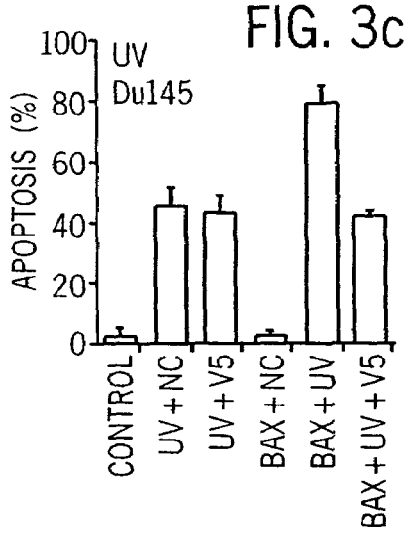
Figure 3D:
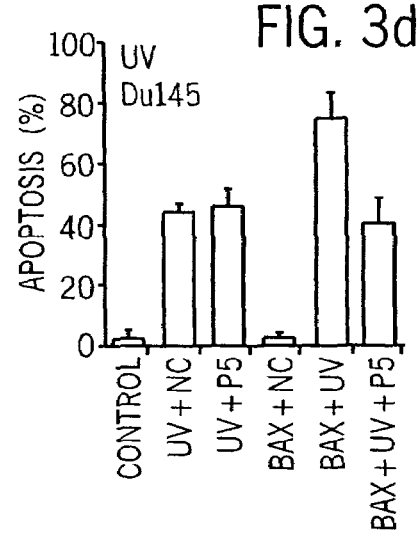
Figure 3E:
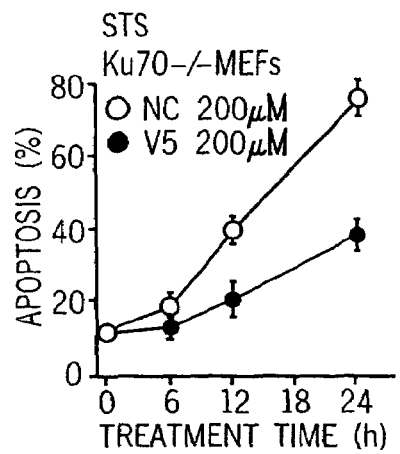
Figure 3F:
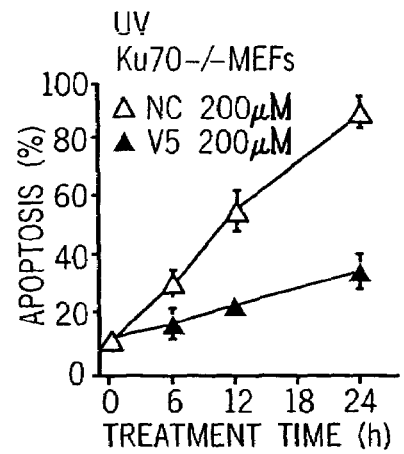

BIPs inhibit various apoptotic stimuli mediated by Bax. BIPs showed anti-apoptotic activities at the concentration of 50 uM–200 uM (FIG. 1E), as well as z-VAD-fmk (Caspase inhibitor) does. Pretreatment of the cells with BIPs for 1 hour was sufficient to protect them from STS- and UVC-induced apoptosis in HeLa cells (FIGS. 2A, B). To be noted, BIPs retained the ability to suppress apoptosis for three days in the culture medium (FIGS. 2A, B). As shown in FIG. 2C, BIP did not enhance z-VAD-fmk's suppression of apoptosis induced by UVC-irradiation as well as STS (not shown). Since BIP inhibits Bax upstream of caspase activation, BIP may not be able to exert an effect additive to that of a caspase-inhibitor. BIPs also suppressed apoptosis induced by anti-cancer drugs (etoposide, cisplatin, and doxorubicin) in cancer cell lines including breast cancer cells (MCF-7), glioma cells (U87-MG), and prostate cancer cells (LNCaP) (FIGS. 2D–L). To confirm that BIP suppresses Bax-mediated apoptosis, the effects of BIPs in Bax-deficient cells (Du145) were examined (FIGS. 3A–D and FIGS. 7A–B). BIPs did not suppress STS- and UVC-induced apoptosis in Bax-deficient cells, whereas BIP showed anti-apoptotic activity in these cells when Bax expression was restored by plasmid transfection (FIGS. 3A–D). These results suggest that BIP specifically inhibits a Bax-mediated signal in apoptosis. These results are consistent with the observations that Ku70 did not show cytoprotection against STS and UVC-irradiation in Bax-deficient cells, and that Ku70 did not block Bak-induced apoptosis. Similarly, BIPs did not suppress Fas- and TRAIL-induced apoptosis (not shown). Fas and TRAIL can trigger a mitochondria-independent cell death pathway, therefore, BIP may not be able to suppress apoptosis induced by these factors. These results suggest that BIP suppresses only Bax-mediated apoptosis. On the other hand, BIP suppressed STS- and UVC-induced apoptosis in Ku70-deficient mouse embryonic fibroblasts (MEFs), suggesting that BIP does not require endogenous Ku70 to suppress Bax-mediated apoptosis (FIGS. 3E, F).

Figure 4A:
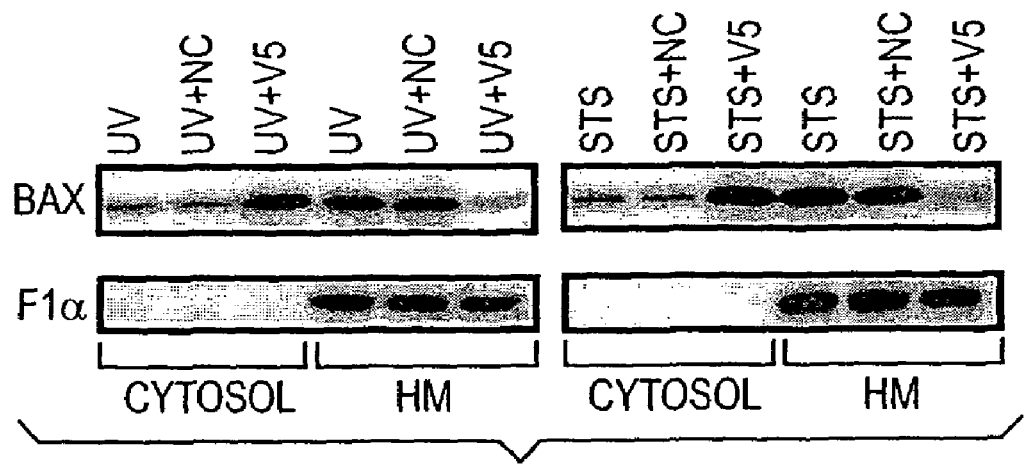
FIGS. 4A–F demonstrate that BIP inhibits the mitochondrial translocation of Bax (A, B).
Figure 4B:
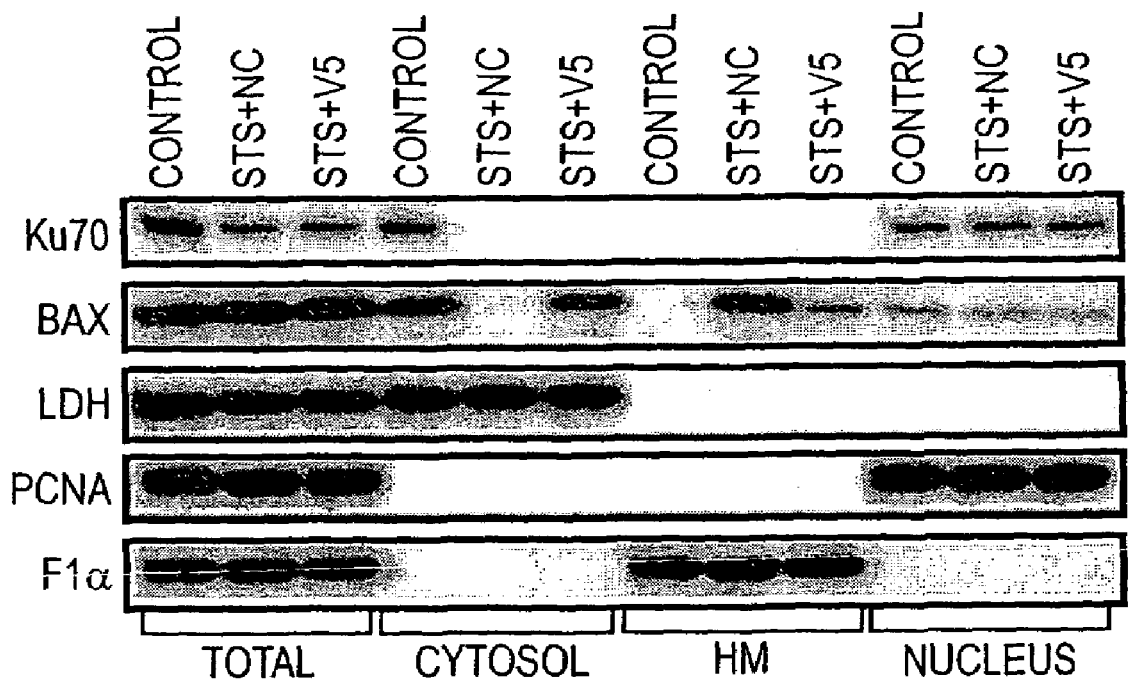
Figure 4C:
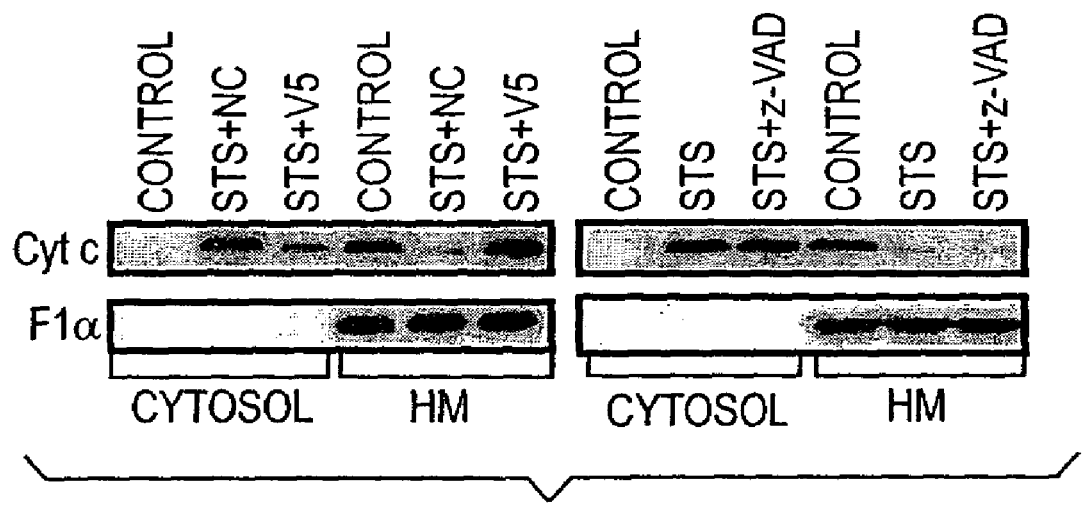
Figure 4E:
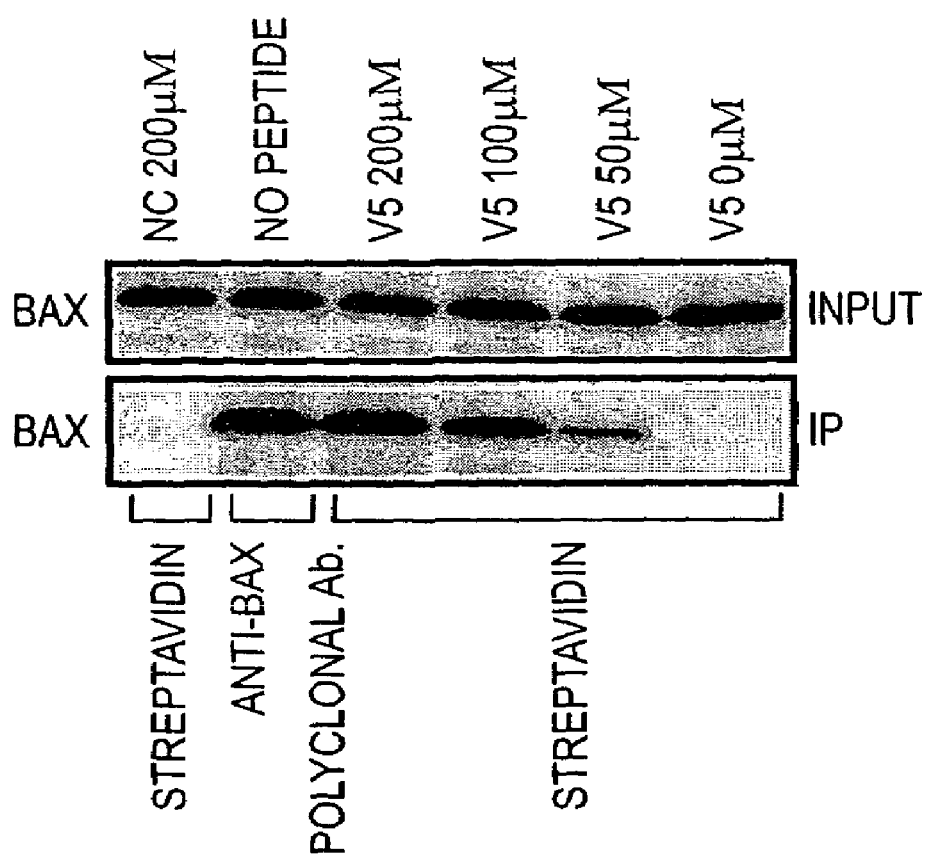
Figure 4D:
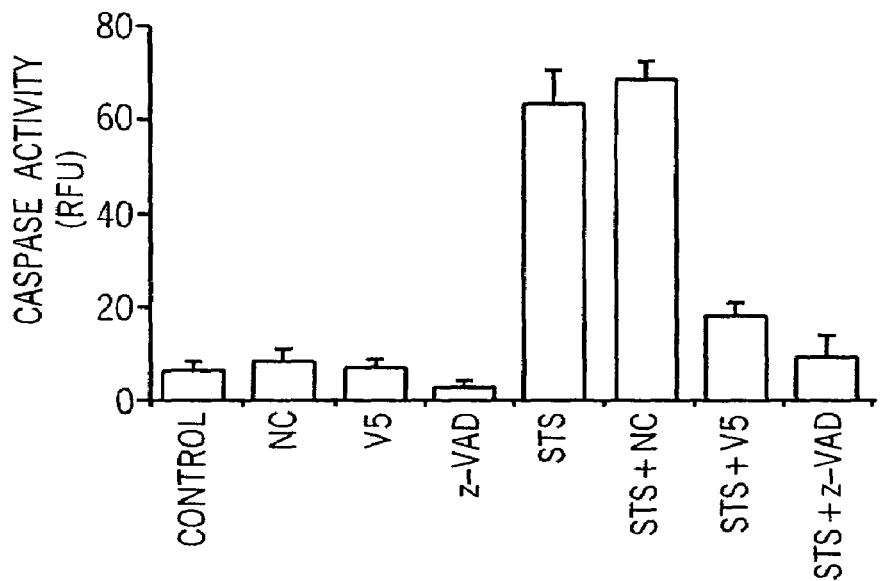
Figure 4F:
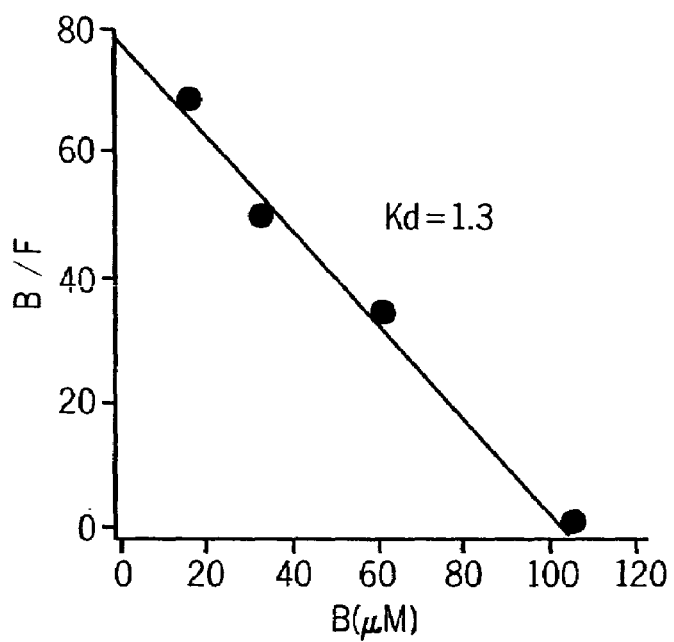

BIP interacts with Bax, and inhibits the mitochondrial translocation of Bax. BIP suppressed the mitochondrial translocation of Bax stimulated by STS and UVC-irradiation (FIG. 4A), as well as Ku70 protein did. As reported in another article, apoptotic stimuli decreased Ku70 levels in the cytosol. BIP did not inhibit this Ku70 disappearance, suggesting that the anti-apoptotic activity of BIP is not due to the inhibition of the degradation of endogenous Ku70. The release of cytochrome c from mitochondria and Caspase activation triggered by apoptotic stimuli were also significantly suppressed by BIP (FIGS. 4C, D), further supporting that BIP protects cells by inhibiting Bax-mediated mitochondria-dependent apoptosis pathway. The interaction of BIP and Bax was confirmed by experiments using the system of biotin-labeled BIP and streptavidin beads. Biotin-labeled BIP (biotin-VPMLK; SEQ ID NO: 1), but not negative control peptide (biotin-IPMIK; SEQ ID NO: 5) precipitated Bax from the cell lysates when the streptavidin beads were added to the samples. On the other hand, Bak was not precipitated by biotin-VPMLK (SEQ ID NO: 1) (FIG. 7E), indicating that BIP binds specifically to Bax, but not Bak. The reason why IPMIK (SEQ ID NO: 5) (negative control (NC) peptide in the figures) did not suppress Bax-mediated cell death is that this modified peptide fails to interact with Bax. The value of Kd for the interaction of BIP and Bax was 1.3 uM when Scatchard analysis was performed using FITC-labeled BIP (VPMLK; SEQ ID NO: 1) and endogenous Bax in Ku70-deficeint MEF cell lysates (FIG. 4F).

The cells treated with FITC-labeled BIP (VPMLK; SEQ ID NO: 1) localized mostly in the cytosol in HeLa cells, but distributed in both the cytosol and the nucleus in Bax-deficient Du145 cells. Bax expression in Du145 cells increased the cytosolic FITC-BIP, suggesting that BIP binds the cytosolic Bax. Co-localization of Bax and BIP was also observed. These results further support that BIP inhibits Bax-mediated apoptosis by interacting with Bax in the cytosol. It is suggested that the conformational change (the N-terminus exposure) of Bax occurs before its mitochondrial translocation and that Ku70 inhibits this event. The monoclonal antibody clone 6A7 is known to detect exposure of the N-terminus of Bax. BIP reduced the amount of Bax protein recognized by 6A7 antibody in the cells treated by apoptotic stimuli, suggesting that BIP inhibits the conformational change of Bax in the same way as Ku70.

Figure 6A:
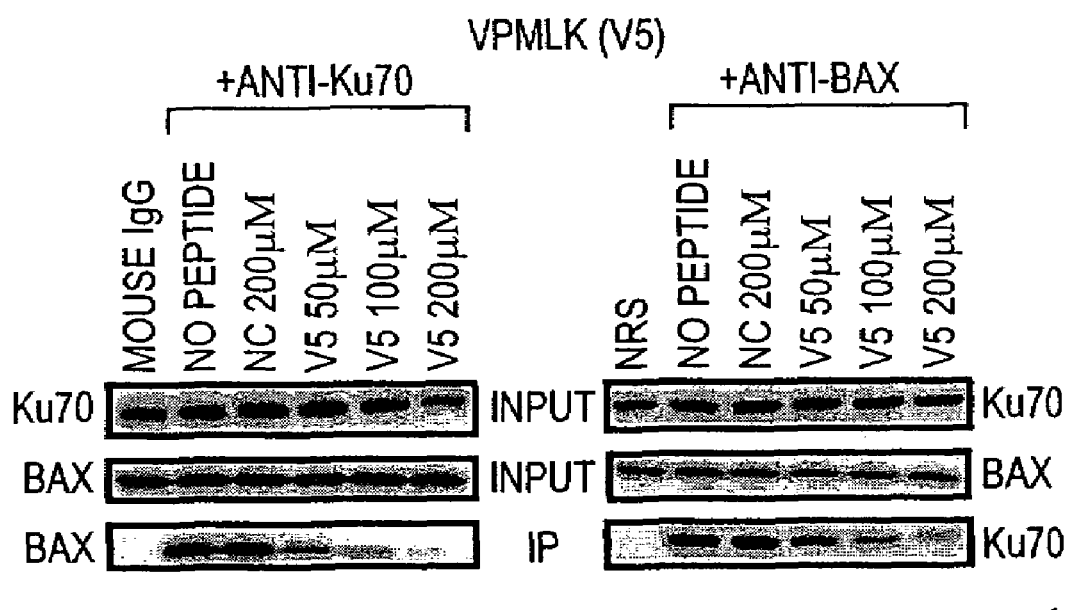
FIGS. 6A–D demonstrate that Ku70-derived peptides bind Bax and dissociate Ku70 from Bax.
Figure 6B:
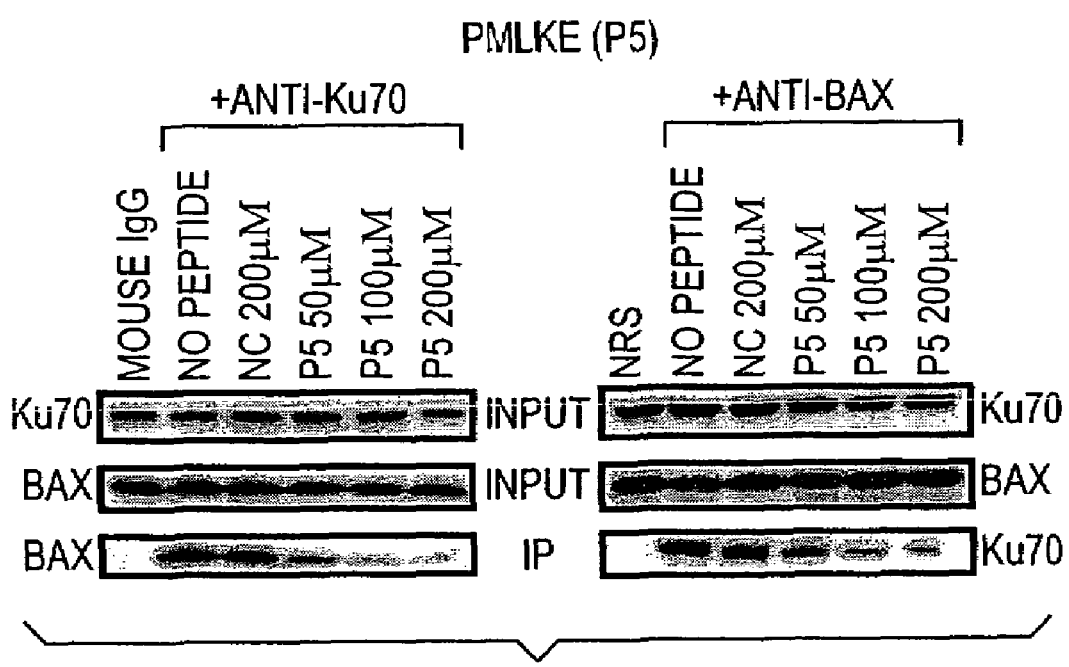
Figure 6C:
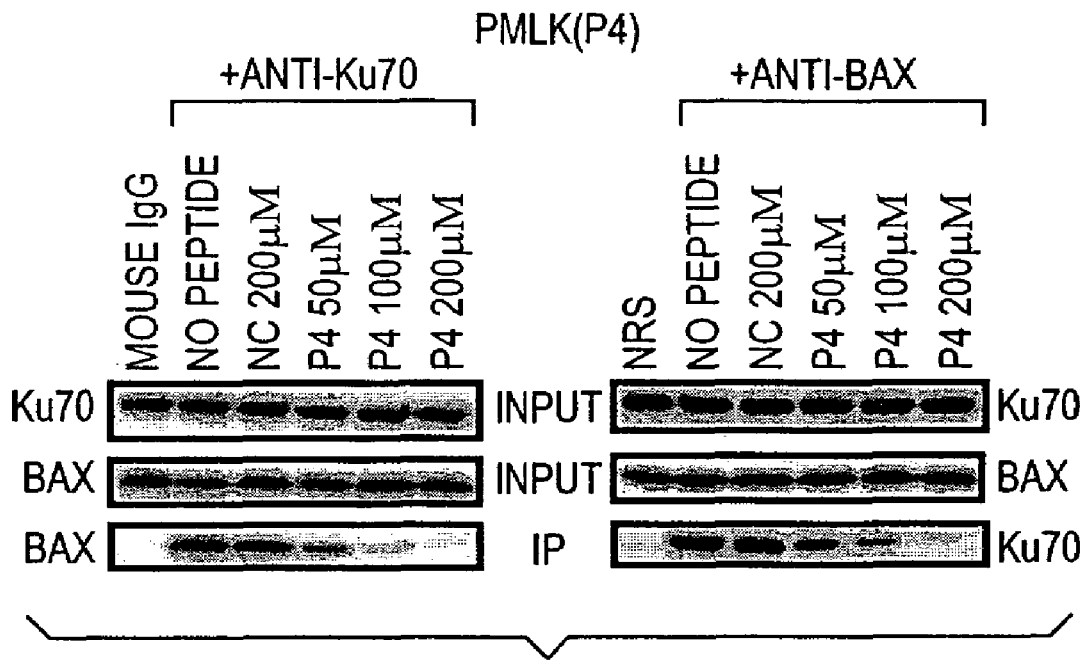
Figure 6D:
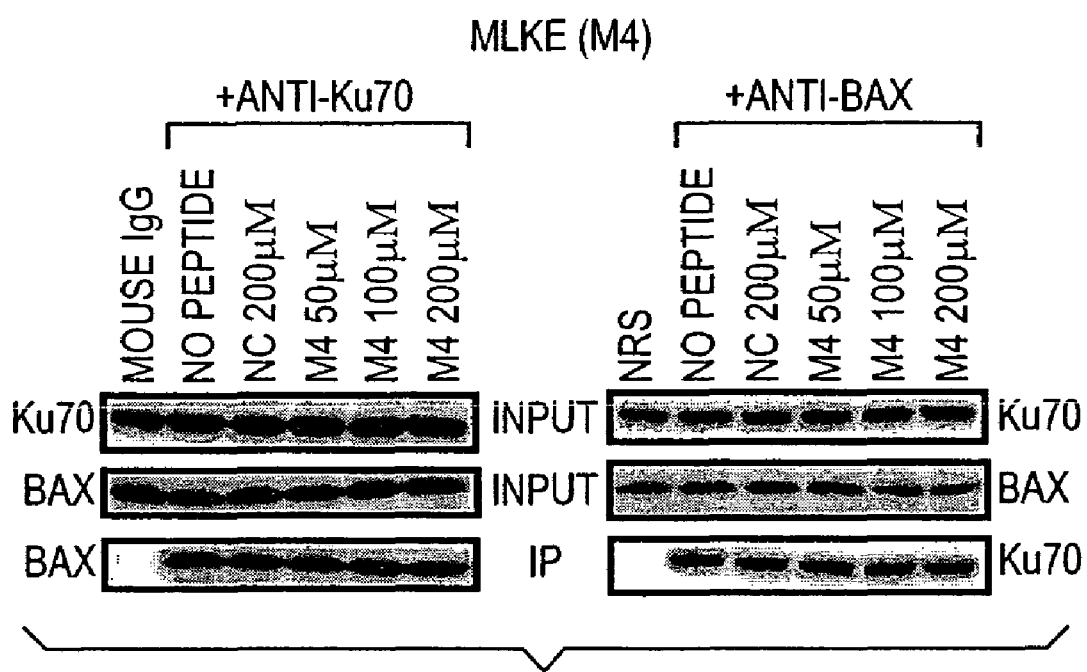
Figure 7A:
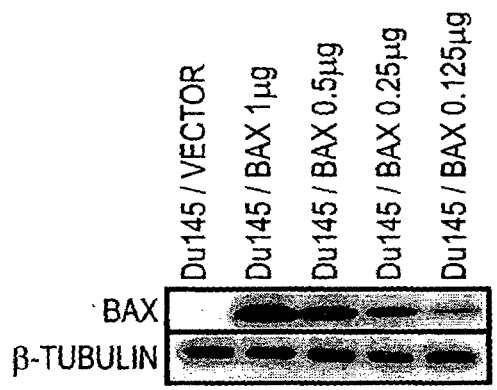
FIG. 7A: Bax-deficient Du145 cells ($10^6$ cells) were transfected with 1.0 ug of pcDNA3-control vector (Du145/Vector) or pcDNA3-Bax (Du145/Bax) at the indicated concentrations. Twenty-four hours later, cells were collected and the levels of Bax as well as β-Tubulin were examined using total cell lysates (20 ug protein/lane).
Figure 7D:
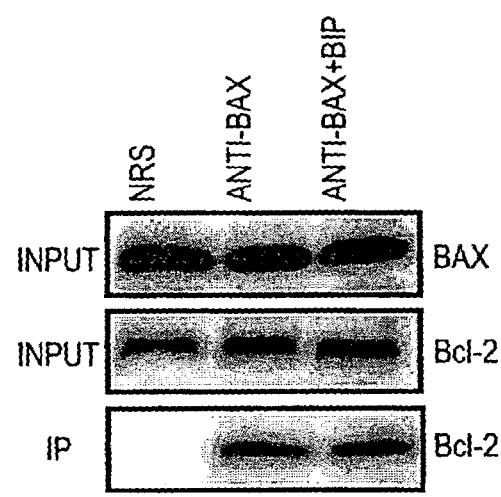
FIG. 7D: BIP does not affect Bax/Bcl-2 heterodimerization. HEK293T cells ($10^7$ cells) were lysed in NP40 buffer and immunoprecipitation was performed with anti-Bax rabbit polyclonal antibody in the presence (Anti-Bax+BIP) or absence (Anti-Bax) of 200 uM V5 peptide using NP40 buffer as described in a previous report (Hsu and Youle, *J. Biol. Chem.* 23:10777–10783, 1998). Pre-immune rabbit serum (NRS) was used as a negative control. Western blot analyses of pre-immunoprecipitation (Input) and immunoprecipitated samples (IP) were performed by anti-Bax mouse monoclonal antibody or anti-Bcl-2 mouse monoclonal antibody.
Figure 7C:
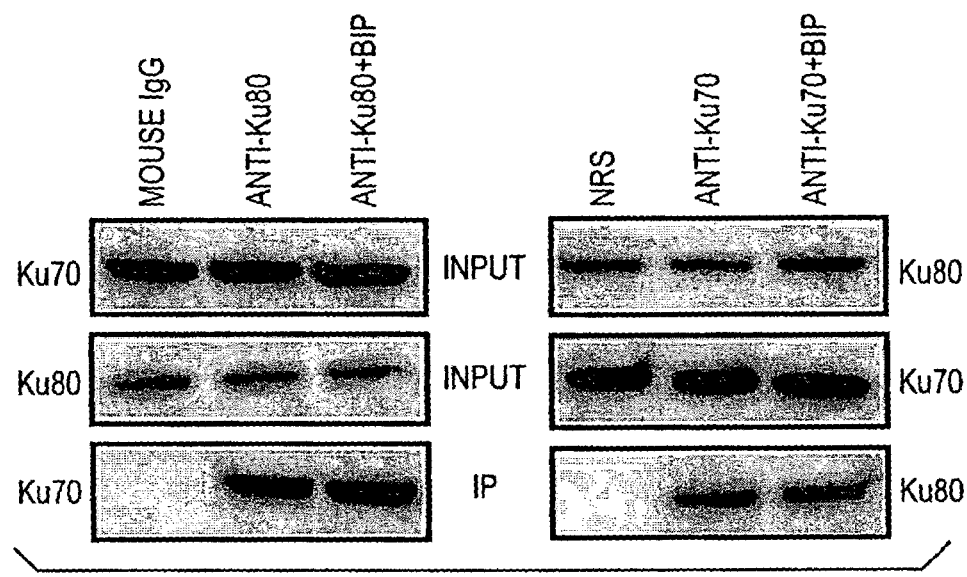
FIG. 7C: BIP does not interfere the interaction of Ku70/Ku80. HEK293T cells ($10^7$ cells) were lysed in CHAPS buffer and immunoprecipitation was performed with anti-Ku80 mouse monoclonal antibody or anti-Ku70 rabbit polyclonal antibody in the presence (Anti-Ku80+BIP) or absence (Anti-Ku80) of 200 uM V5 peptide using CHAPS buffer as described in Methods. Pre-immune rabbit serum (NRS) and mouse IgG were used as negative controls. Western blot analyses of pre-immunoprecipitation (Input) and immunoprecipitated samples (IP) were performed by anti-Ku70 rabbit polyclonal antibody or anti-Ku80 mouse monoclonal antibody.
Figure 7E:
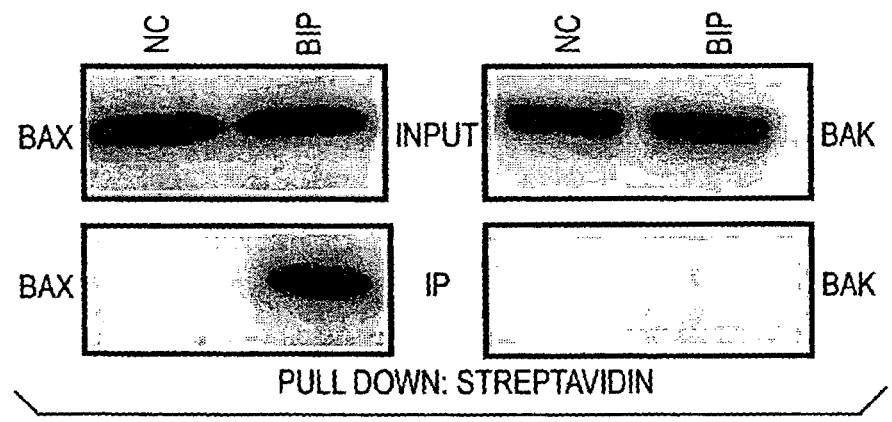
FIG. 7E: BIP does not interact with Bak. HEK293T cells ($10^7$ cells) were lysed in CHAPS buffer in the presence of 200 uM biotin-labeled negative control (NC) peptide or biotin-labeled V5 peptide (BIP). Co-precipitation was performed with streptavidin beads using CHAPS buffer as described in Methods. Western blot analyses of pre-precipitation (Input) and precipitated samples (IP) were performed by anti-Bax polyclonal antibody or anti-Bak polyclonal antibody.
Figure 7B:
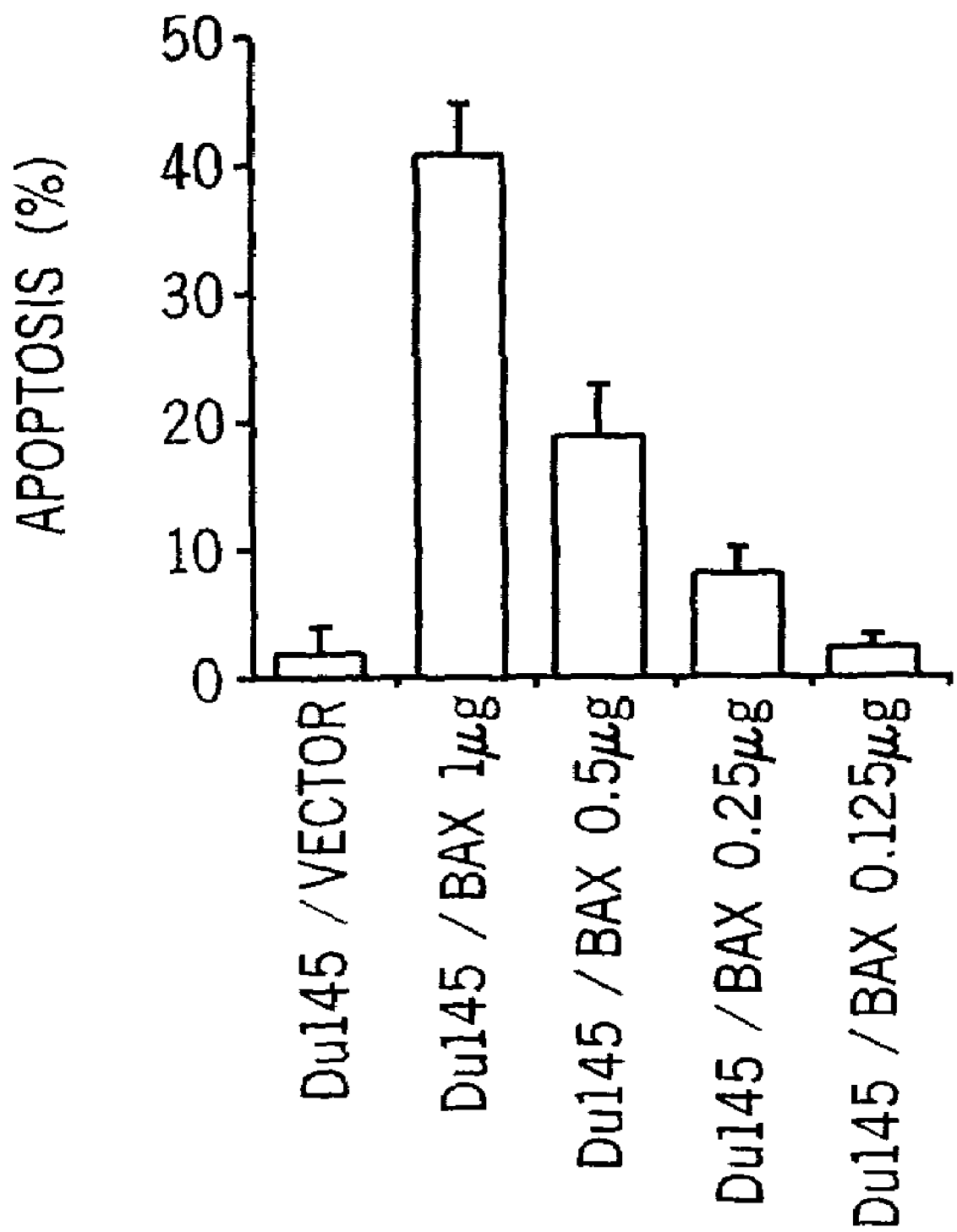
FIG. 7B: All the cells in FIG. 1A were also co-transfected with 0.5 ug pEGFP for the marking of transfected cells. Apoptosis in the transfected cells was analyzed 24 hours following transfection with Hoechst dye staining of the nucleus as described in Methods. The concentration of 0.125 ug ($10^6$ cells) was chosen to restore non-toxic levels of Bax in Du145 cells.

Inhibition of the interaction between endogenous Ku70 and Bax by peptides. BIP (VPMLK (V5; SEQ ID NO: 1) and PMLKE (P5; SEQ ID NO: 2)) inhibited the interaction (co-immunoprecipitation) of the endogenous Bax and Ku70 in a dose dependent manner (FIGS. 6A, B). On the other hand, BIP did not interfere with the interaction of Ku70/Ku80 or Bax/Bcl-2 heterodimerization (FIGS. 7A–B). These results suggest that BIP specifically interacts with Bax through the Ku70-binding domain in Bax, and that BIP competes with Ku70 to bind Bax. Interestingly, PMLK (P4;

SEQ ID NO: 3) inhibited the interaction of Bax and Ku70 when it was added into the cell lysates (FIG. 6C), although PMLK (P4; SEQ ID NO: 3) could not suppress apoptosis in the cell culture. On the other hand, MLKE (M4; SEQ ID NO: 6) did not interfere with Bax-Ku70 interaction (FIG. 6D). These results suggest that four amino acids of PMLK (SEQ ID NO: 3) may be sufficient to bind Bax at least in cell lysate. As shown in FIG. 1, VPMLK (SEQ ID NO: 1) and PMLKE (SEQ ID NO: 2) were able to suppress Bax-induced apoptosis. Although further analysis is required, failure of PMLK (SEQ ID NO: 3) to suppress apoptosis in the culture may be the result of rapid degradation, modification, or escape of this peptide in the living cells. It is also possible that addition of V (N-terminus) or E (C-terminus) to PMLK (SEQ ID NO: 3) may improve the membrane permeability or the cytosolic retention of the peptide. Future biochemical study may answer this question.

In summary, we have identified membrane permeable peptides (BIPs) derived from the Bax-binding domain of Ku70 that inhibit Bax-mediated apoptosis. We also found that BIP inhibits exposure of the N-terminus of Bax induced by apoptotic stimuli. The mechanism of the activation process of Bax is still enigmatic. BIP may become a new tool to elucidate the mechanism of the conformational change of Bax. At present, it is unclear whether BIP can bind Bax directly. The possibility remains that other factors are involved in this interaction. Future biochemical study analyzing the complex formation of purified inactive Bax proteins and peptides may answer these questions. Bax-mediated cell demise is known to be involved in several types of degenerative diseases and in loss of viability of the cultured cells (Wolter, et al., *J. Cell Biol.* 139:1281–1292, 1997; Saito, et al., *Nat. Cell Biol.* 2:553–555, 2000; Korsmeyer, et al., *Cell Death Differ.* 7:1166–1173, 2000). The membrane permeable Bax-inhibiting peptides developed in this study may provide information leading to development of new therapeutics that act by regulating apoptosis.

Methods

Cell Culture and Apoptosis Detection

HEK293T and HeLa cells were cultured in MEM supplemented with 10% fetal bovine serum (FBS) and Du145 cells and mouse embryonic fibroblasts (MEFs) were in DMEM with 10% FBS. Transfection of the plasmids was performed by SuperFect (Qiagen) according to the manufacturer's manual. Apoptosis was induced by pcDNA3-human Bax (Bax-encoding plasmid)-transfection, Staurosporin (STS)-treatment and UVC-irradiation. The amount of the plasmids, the concentration of STS, and the energy of UVC-irradiation are described in the figure legends. Apoptosis in the transfected cells was analyzed as follows: A plasmid encoding enhanced green fluorescent protein (EGFP) (0.5 ug to $10^6$ cells) was transfected to all the groups to mark the transfected cells. After the treatment, cells were stained with Hoechst dye and cells with apoptotic nuclei were counted in GFP-expressing cells under the fluorescent microscope as described by Matsuyama, et al., *J. Biol. Chem.* 273:30995–31001, 1998. Each point in the figures showing percentages of apoptosis represents the mean +/−SE of three experiments. Caspase activities of cells were measured by detecting the cleavage of fluorogenic substrate of Caspase (DEVD-afc) as previously described.

Plasmids

The plasmid pcDNA3-Bax (human) has been described. (Xu and Reed, *Mol. Cell* 1:337–346, 1998). The plasmid vectors pCMV-2B and pEGFP were purchased from Stratagene and Clonetech, respectively, and human full-length Ku70 and the deletion mutants of Ku70 were subcloned into BamH1 and Sal1 sites of pCMV-2B vector, and the deletion mutants of Bax were subcloned into EcoR1 and Xho1 sites of pEGFP plasmid. The full-length Ku70 cDNA was prepared by RT-PCR using HeLa cell cDNA. The mutant constructs of Ku70 described in this article were prepared by $2^{nd}$ step PCR mutagenesis method (Xu and Reed, supra, 1998).

Delivery of Peptide into the Cells

For the membrane permeable peptide, the stock solution was prepared with PBS, and the peptides were directly added into medium and incubated for 1 hour or for the periods of time indicated in the figure legends (FIG. 2A, B) at 37° C. before apoptosis induction. Non-membrane permeable peptide was delivered using BioPorter reagent (Gene Therapy Systems) according to the manufacturer's manual. BioPorter-based peptide delivery was performed 4 hours before apoptosis induction.

Cytochrome c Detection

One day following the transfection of the plasmids or the treatment of the cells with STS or UVC-irradiation, cells were re-suspended in 200 ul of homogenization buffer (250 mM Sucrose, 20 mM HEPES, pH 7.5, 10 mM KCl, 1.5 mM $MgCl_2$, 1 mM EDTA, 0.1 mM phenylmethylsulfonyl fluoride), and separation of the cytosol and heavy membrane fraction (containing mitochondria and ER) were performed as previously reported[14, 15]. Cytosolic fraction of 20 ug protein and 1 ul of membrane fraction (out of total 50 ul) were analyzed by Western-blot with cytochrome c antibody (BD-Pharmingen dilution 1:1000).

Immunoprecipitation

Endogenous protein: HEK293T ($10^7$ cells) were lysed in 200 ul of "CHAPS-based buffer" (150 mM NaCl, 10 mM Hepes, pH 7.4, 1.0% CHAPS) containing protease inhibitors (100 times dilution of Protease Inhibitors Cocktail; Sigma) according to the previously reported method (Hsu and Youle, *J. Biol. Chem.* 273:10777–10783, 1998). After pre-cleaning of 600 ul of the sample with 50 ul of Protein G-Sepharose at 4° C. for 1 hour, immunoprecipitations were performed by incubating 200 ul of lysates with 20 ul of Protein G-Sepharose preabsorbed with 2 ug of anti-Bax polyclonal (BD-Pharmingen) or anti-Ku70 monoclonal antibody (BD-Pharmingen) at 4° C. for 2 hours. In some cases, 2 ug of anti-Bax monoclonal antibody (clone 6A7, BD Pharmingen) was used to detect active form of Bax. After extensive washing in the buffer, beads were boiled in 40 ul of Laemmli buffer and 20 ul of the eluted proteins were subjected to SDS-PAGE. *Co-precipitation of biotin-labeled peptides and endogenous Bax using streptavidin beads*: HEK293T cells ($10^7$ cells) lysed in 200 ul CHAPS-based buffer were incubated with biotin-labeled negative control (NC) peptide or VPMLK (V5; SEQ ID NO: 1) peptide for 1 hour. The concentrations of NC and V5 peptide labeled with biotin are described in the figure legends. Co-precipitation was performed with streptavidin beads prepared in a ratio of 75% Streptavidin Sepharose to 25% CHAPS buffer according to the manufacturer's manual (Amersham Pharmacia Biotech). *Flag-tagged-Ku 70 and endogenous Bax*: HEK293T cells ($10^6$ cells) were co-transfected with 1.0 ug of pcDNA3-Bax and 1.0 ug of pCMV-2B-control vector (Flag-tagged firefly luciferase), pCMV-2B-Ku70 wt (Flag-Ku70 wt), pCMV-2B-Ku70$_{1-577}$ (Flag-Ku70$_{1-577}$), or pCMV-2B-Ku70$_{578-609}$(Flag-Ku70$_{578-609}$) in the presence of 50 uM z-VAD-fmk. Co-immunoprecipitation was performed with anti-Flag monoclonal antibody (Stratagene; 2 ug for 200 ul sample), and Western-blot of Bax (15% SDS-PAGE) was done with anti-human Bax polyclonal antibody (BD-Phramingen).

Subcellular Fractionation

One day after the treatment, cells were homogenized (Teflon homogenizer) with 200 ul of ice-cold homogenization buffer (250 mM Sucrose, 20 mM HEPES, pH 7.5, 10 mM KCl, 1.5 mM $MgCl_2$, 1 mM EDTA, 0.1 mM phenylmethylsulfonyl fluoride). Subcellular fractionation was performed as reported (Hoetelmans, et al., *Cell Death Differ.* 7:384–392, 2000), together with the confirmation of each fraction with appropriate marker proteins (cytosolic fraction; Lactate dehydrogenase (LDH) by anti-human LDH antibody (Sigma), nucleus fraction; PCNA by anti-PCNA antibody (Oncogene), mitochondria containing heavy membrane fraction; F1-ATPase α-subunit by anti-F1α subunit antibody (Molecular Probe). For total cell lysates, samples were prepared with ice-cold lysis buffer (containing 50 mM NaCl, 25 mM Hepes (pH 7.4), 1 mM EDTA, 1 mM EGTA, 1 mM PMSF, 10 ug/ul E-64, and 1% Triton X-100). In some experiments, samples containing 20 ug of protein from total cell lysates or cytosolic fraction were subjected to Western analysis of Bax or Ku70. The pellets of the fractions of heavy membrane and nucleus were dissolved in 50 ul of Laemmli buffer and the same proportion of the volume equal to that of the cytosol samples out of its total volume was used for Western-blot analysis.

Fluorescent Microscope Image

HeLa cells and transfected or untransfected Du145 cells with pcDNA3-Bax were incubated with 200 uM FITC-labeled VPMLK (V5; SEQ ID NO: 1) peptide for 1 hour prior to microscopic analysis by fluorescent microscope. For immunostaining, cells incubated with FITC-V5 peptide for 1 hour were fixed with 4% paraformaldehyde in phosphate buffered saline (PBS). Cells were permeablized with 0.5% Triton X-100 and 0.05% Tween-20 in PBS. Fixed cells were incubated in PBS containing 5% BSA at 37 C, and stained with anti-Bax monoclonal antibody (BD-Pharmingen, dilution 1:50) followed by the detection of Texas-Red labeled anti-mouse IgG (Jackson ImmunoResearch, dilution 1:100).

Scatchard Analysis of the Binding of FITC-V5 and Bax

Ku70-deficient MEFs ($10^7$ cells) were lysed in 200 ul of "detergent-free hypotonic buffer" (hypotonic (5 mM NaCl) phosphate buffered saline, pH 7.4) containing protease inhibitors (100 times dilution of Protease Inhibitors Cocktail; Sigma) according to the previously reported method (Hsu and Youle, supra, 1998). For Scatchard analysis, the cytosol fraction was used and NaCl was added to prepare the isotonic condition before immunoprecipitation as previously reported (Hsu and Youle, supra, 1998). After incubating the sample with various concentrations such as 25, 50, 100, and 200 uM of FITC-labeled VPMLK (V5; SEQ ID NO: 1) peptide at 37° C. for 1 hour, immunoprecipitations were performed in detergent free condition at 37° C. by incubating 200 ul of lysates with 20 ul of Protein G-Sepharose preabsorbed with 2 ug of anti-Bax antibody for 2 hours. FITC fluorescence of pre-immunoprecipitation ("B"+"F") and the supernatant following immunoprecipitation ("F") were measured by fluorescence microplate reader (Molecular Devices), and the values of "B+F" and "B" were calculated. Kd was calculated by Scatchard plot. For control experiment, immunodepletion of Bax was performed before the incubation of FITC-V5 and cell lysates. Two hundred ul of cell lysates were mixed with 4 ug of anti-Bax antibody and incubated at 37° C. for 2 hours for immunodepletion of Bax. No significant binding of FITC-V5 to the cellular components was detected in Bax-immunodepleted samples.

I claim:

1. A method of protecting cells from cell death comprising administering to the cell an effective amount of a composition comprising a Ku70-derived Bax-inhibiting peptide, wherein the peptide comprises a peptide selected from the group consisting of SEQ ID NO: 7, SEQ ID NO: 1 and SEQ ID NO:2.

2. The method of claim 1, wherein the peptide comprises SEQ ID NO: 7.

3. The method of claim 1, wherein the peptide comprises SEQ ID NO: 1.

4. The method of claim 1, wherein the peptide comprises SEQ ID NO: 2.

5. The method of claim 1, wherein the Ku70-derived Bax-inhibiting peptide is administered to a patient.

6. The method of claim 5, wherein the patient is a stroke patient.

7. The method of claim 5, wherein the patient is a heart attack patient.

8. The method of claim 5, wherein the patient is an isehemia patient.

9. The method of claim 5, wherein the patient is a degenerative disease patient.

10. The method of claim 5, wherein the patient has an infection cause by an agent selected from the group consisting of bacteria, viruses and protozoa.

11. The method of claim 5, wherein the patient exhibits side effects from anticancer drugs or UV/X-ray irradiation.

* * * * *